US010302545B2

(12) United States Patent
Crow et al.

(10) Patent No.: US 10,302,545 B2
(45) Date of Patent: May 28, 2019

(54) AUTOMATED DROP DELAY CALCULATION

(71) Applicant: BECTON, DICKINSON AND COMPANY, Franklin Lakes, NJ (US)

(72) Inventors: Matthew J. Crow, Shoreline, WA (US); Daniel Horner, Seattle, WA (US)

(73) Assignee: BECTON, DICKINSON AND COMPANY, Franklin Lakes, NJ (US)

(*) Notice: Subject to any disclaimer, the term of this patent is extended or adjusted under 35 U.S.C. 154(b) by 0 days.

(21) Appl. No.: 15/761,011

(22) PCT Filed: Oct. 3, 2016

(86) PCT No.: PCT/US2016/055217
§ 371 (c)(1),
(2) Date: Mar. 16, 2018

(87) PCT Pub. No.: WO2017/062319
PCT Pub. Date: Apr. 13, 2017

(65) Prior Publication Data
US 2018/0284007 A1    Oct. 4, 2018

Related U.S. Application Data

(60) Provisional application No. 62/237,306, filed on Oct. 5, 2015.

(51) Int. Cl.
*G01N 15/14* (2006.01)
*G01N 15/10* (2006.01)

(52) U.S. Cl.
CPC ..... *G01N 15/1404* (2013.01); *G01N 15/1459* (2013.01); *G01N 15/1463* (2013.01);
(Continued)

(58) Field of Classification Search
CPC ..... G01N 2015/149; G01N 2015/1006; G01N 15/1459; G01N 15/1404;
(Continued)

(56) References Cited

U.S. PATENT DOCUMENTS 3,775,058 A    11/1973  Bush
4,284,496 A    8/1981   Newton
(Continued)

FOREIGN PATENT DOCUMENTS

EP    1418409    4/2006
EP    2241907    10/2010
(Continued)

OTHER PUBLICATIONS

Lansdorp, et al. "Optical Monitoring for measuring the amplitude and phase of perturbations on the surface of a capillary jet in a high-speed cell sorter" Review of Scientific Instruments 75(3); 741-746, 2004.
(Continued)

*Primary Examiner* — Michael P Stafira
(74) *Attorney, Agent, or Firm* — Khin K. Chin; Bret E. Field; Bozicevic, Field & Francis LLP

(57) ABSTRACT

Aspects of the present disclosure include methods and systems for determining drop delay of a flow stream in a flow cytometer. Methods according to certain embodiments include obtaining a first frequency (f1) of drop perturbation of a flow stream subjected to an oscillating vibration, capturing one or more images of the flow stream in a detection field, obtaining a second frequency (f2) of drop perturbation of the flow stream based on one or more of the captured images and determining the drop delay of the flow stream based on the first frequency and the second frequency. Systems for practicing the subject methods having an imaging sensor for capturing one or more images of the flow stream and a processor configured to calculate drop delay using one or more of the captured images are also provided. Non-transitory computer readable storage mediums are also described.

14 Claims, 7 Drawing Sheets

(52) U.S. Cl.
CPC ............... *G01N 2015/1006* (2013.01); *G01N 2015/1406* (2013.01); *G01N 2015/149* (2013.01)

(58) Field of Classification Search
CPC ........... G01N 2015/1406; G01N 15/14; G01N 15/1425; G01N 2015/1481; G01N 15/1427; G01N 15/1429; G01N 15/1463; G01N 2015/1415; G01N 2333/161; G01N 33/56972; G01N 33/56983; G01N 33/56988; G01N 2015/0065; G01N 2015/144; G01N 33/5005; G01N 15/1434; G01N 15/147; G01N 15/1475; G01N 1/08; G01N 2015/0019; G01N 2015/1075; G01N 2015/1438; G01N 2015/1477; G01N 21/27; G01N 33/582; G01N 15/1436; G01N 15/1484; G01N 1/30; G01N 2001/302; G01N 2015/1402; G01N 2015/1452; G01N 2015/1488; G01N 2015/1493; G01N 21/00; G01N 21/01; G01N 21/39; G01N 2201/06113; G01N 2201/0846; G01N 2333/405; G01N 33/49; G01N 33/5097; G01N 33/52; G01N 33/56961; G01N 35/00871; G02F 1/136286; G02F 1/1368; G02F 1/134309; G02F 1/13624; G02F 1/13454; G02F 2001/13606; G02F 2201/124; G02F 1/0121; G02F 2203/18; G01J 11/00; G02B 27/48
See application file for complete search history.

(56) References Cited

U.S. PATENT DOCUMENTS

| | | |
|---|---|---|
| 4,487,320 A | 12/1984 | Auer |
| 4,691,829 A | 9/1987 | Auer |
| 5,101,113 A | 3/1992 | Hirleman et al. |
| 5,150,313 A | 9/1992 | Van Den et al. |
| 5,407,794 A | 4/1995 | Kass |
| 5,466,572 A | 11/1995 | Sasaki et al. |
| 5,475,487 A | 12/1995 | Mariella, Jr. et al. |
| 5,483,469 A | 1/1996 | Van Den et al. |
| 5,489,506 A | 2/1996 | Crane |
| 6,003,678 A | 12/1999 | Van Den et al. |
| 6,211,477 B1 | 4/2001 | Cardott et al. |
| 6,372,506 B1 | 4/2002 | Norton |
| 6,589,792 B1 | 7/2003 | Malachowski |
| 6,819,411 B1 | 11/2004 | Sharpe et al. |
| 7,362,424 B2 | 4/2008 | Van Den et al. |
| 7,639,358 B2 | 12/2009 | Kanda |
| 7,679,039 B2 | 3/2010 | Van Den et al. |
| 7,728,974 B2 | 6/2010 | Van Den et al. |
| 9,200,334 B2 | 12/2015 | Van Den et al. |
| 2002/0034748 A1 | 3/2002 | Quake et al. |
| 2002/0119558 A1 | 8/2002 | Seidel et al. |
| 2002/0167656 A1 | 11/2002 | Van Den et al. |
| 2002/0186375 A1 | 12/2002 | Ashbury et al. |
| 2005/0078299 A1 | 4/2005 | Fritz et al. |
| 2005/0112541 A1 | 5/2005 | Durack et al. |
| 2006/0002824 A1 | 1/2006 | Chang et al. |
| 2006/0263829 A1 | 11/2006 | Evans et al. |
| 2007/0117086 A1 | 5/2007 | Evans et al. |
| 2007/0269348 A1 | 11/2007 | Van Den et al. |
| 2008/0024758 A1 | 1/2008 | Tabata |
| 2008/0213915 A1 | 9/2008 | Durack et al. |
| 2008/0259342 A1 | 10/2008 | Van Den et al. |
| 2009/0107893 A1 | 4/2009 | Schembri et al. |
| 2009/0176271 A1 | 7/2009 | Durack et al. |
| 2010/0273208 A1 | 10/2010 | Takenaka et al. |
| 2010/0297759 A1 | 11/2010 | Kanda |
| 2010/0314555 A1 | 12/2010 | Muraki |
| 2011/0020855 A1 | 1/2011 | Shinoda |
| 2011/0221892 A1* | 9/2011 | Neckels ............ G01N 15/1427 348/135 |
| 2012/0200857 A1 | 8/2012 | Sharpe et al. |
| 2014/0309782 A1* | 10/2014 | Sharpe ................... G05D 21/02 700/266 |
| 2016/0170168 A1 | 6/2016 | Rohani et al. |

FOREIGN PATENT DOCUMENTS

| | | |
|---|---|---|
| WO | WO1992017288 | 10/1992 |
| WO | WO2010095391 | 8/2010 |
| WO | WO2014151049 | 9/2014 |

OTHER PUBLICATIONS

Osborne, Geoffrey W. "A Method of Quantifying Cell Sorting Yield in 'Real Time'", Cytometry Part A, vol. 77A, No. 10, Jul. 26, 2010, pp. 983-989.

Petersen et al., "Stability of the Breakoff Point in a High-Speed Cell Sorter", Cytometry Part A, vol. 56A, No. 2, pp. 63-70 (2003).

\* cited by examiner

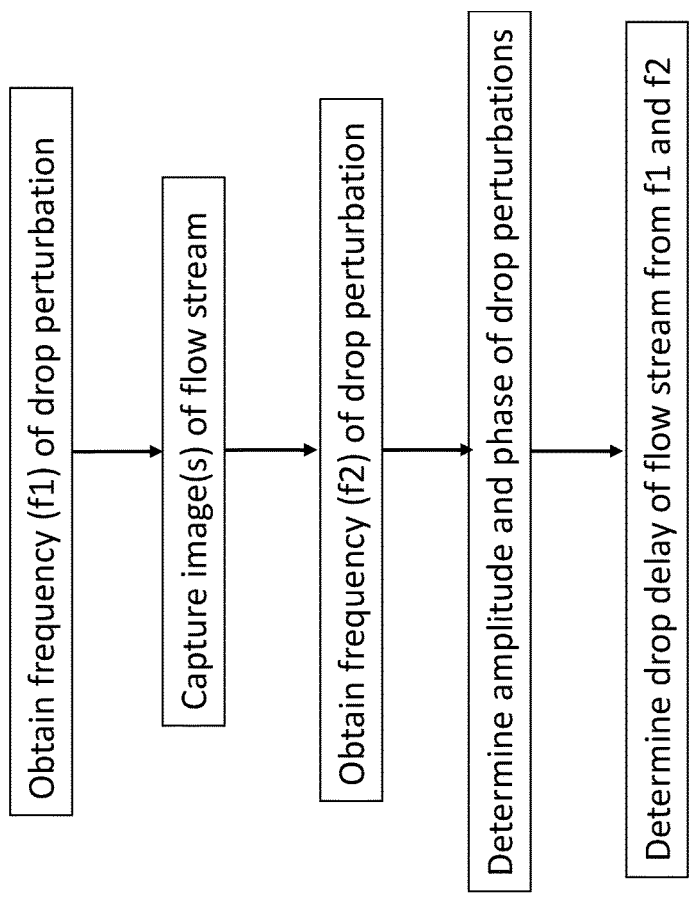

AUTOMATED DROP DELAY CALCULATION

CROSS-REFERENCE TO RELATED APPLICATIONS

This application claims priority to U.S. Provisional Patent Application Ser. No. 62/237,306 filed Oct. 5, 2015, the disclosure of which application is incorporated herein by reference.

INTRODUCTION

Flow cytometers are used for analyzing and sorting particles in a fluid sample, such as cells of a blood sample or particles of interest in any other type of biological or chemical sample. Within a flow cell, a liquid sheath is formed around the particle-containing stream to impart a substantially uniform velocity on the flow stream. The flow stream exits the flow cell via a nozzle with a nozzle diameter that is appropriate for the fluidics system and sort rate desired. The flow cell hydrodynamically focuses the particles (e.g., cells) within the stream to pass through the center of an irradiation source (e.g. laser beam). The intersection at which the particles of interest in the flow stream pass through the irradiation source is often referred to as the interrogation point. As particles of interest (e.g., cells) move through the interrogation point, light from the irradiation source (e.g., laser) is scattered. The light can also excite components in the cell stream that have fluorescent properties, such as fluorescent markers that have been added to the fluid sample and adhered to certain cells of interest.

In flow cytometers that sort cells by an electrostatic method, the desired cells are contained within an electrically charged droplet. To produce droplets, the flow cell is rapidly vibrated by an acoustic device, such as a piezoelectric transducer. The volume of a droplet is conventionally estimated by the hydrodynamic properties of the flow stream and the nozzle dimensions. To charge the droplet, the flow cell includes a charging element. Since the cell stream exits the flow cell in a substantially downward vertical direction, the droplets also propagate in that direction after they are formed. Perturbations in the flow stream, including turbulence caused by the variability in the size of particles present in the flow stream or drift in the flow cytometer components can impact the predictability of whether a drop in the flow stream contains a particle of interest. Inaccurate predictions of droplets that contain particles can be detrimental to qualitative analysis, resulting in imprecise cell sorting, contamination of sorted samples as well as quantitative loss of biological sample.

SUMMARY

Aspects of the present disclosure include methods for determining drop delay of a flow stream in a flow cytometer. Methods according to certain embodiments include obtaining a first frequency (f1) of drop perturbation of a flow stream subjected to an oscillating vibration, capturing one or more images of the flow stream in a detection field, obtaining a second frequency (f2) of drop perturbation of the flow stream and determining the drop delay of the flow stream based on the first frequency and the second frequency. In some embodiments, the second frequency is obtained from a plurality of different drop perturbation frequencies, such as by varying the frequency of the oscillating transducer across a range of frequencies. In embodiments, methods include capturing one or more images of the flow stream in the detection field at each of the different drop perturbation frequencies. In some embodiments, the detection field includes the flow stream upstream from the flow stream break-off point and downstream from the laser irradiation point. In certain embodiments, the second frequency is determined to be the frequency when images of the flow stream at that frequency contain one more distinct drop in the detection field than at the first frequency. In other embodiments, the second frequency is chosen based on maximizing an image similarity metric between a location on the first image and a designated location on the second image. In some embodiments, this location is distinct from the location of break off. In embodiments where the measurement location is offset from the location of droplet breakoff, the determined drop delay is adjusted with a fixed offset term. In some embodiments, images of the flow stream are captured at a moment that is not the instant of droplet breakoff. In those embodiments, the determined drop delay is adjusted with a fixed offset that reflects the difference between the moment of image acquisition and the moment of droplet breakoff.

In other embodiments, the detection field is downstream from a deflection plate and the flow stream is subjected to an electrical charge upstream from the deflection plate such that the first frequency and second frequency are determined from one or more captured images of the deflected flow stream. In these embodiments, methods include capturing one or more images of the flow stream in the detection field downstream from a deflection plate, determining a first frequency and a second frequency from the one or more captured images and determining the drop delay of the flow stream based on the first frequency and second frequency. In some instances, the first frequency is obtained when one or more of the captured images shows a deflection of one or more drops in the detection field. The second frequency may be obtained from a plurality of different drop perturbation frequencies, such as by sweeping across a range of frequencies. In certain instances, the second frequency is determined to be the frequency when one or more of the captured images exhibit a maximal stream deflection in the detection field. In embodiments, the first frequency and the second frequency are determined using the captured images and are not determined based on a detection of current from the charged flow stream drops.

Methods also include, according to some embodiments, determining one or more of the amplitude and phase of drop perturbations in the flow stream at each of the different frequencies. For example, the amplitude and/or phase may be determined by irradiating (e.g., with a laser) a vertical axis of the flow stream subjected to the oscillating vibration, detecting (e.g., with a position sensing detector) first and second light signals along the irradiated flow stream and calculating a differential signal between the first signal and second signal. In these embodiments, methods may also include adjusting one or more of the amplitude and phase of drop perturbations, such as by adjusting the amplitude and/or phase of the oscillating transducer at each of the plurality of frequencies. In certain instances, one or more of the amplitude and phase of drop perturbations are maintained constant during the frequency sweep. In other instances, the phase may be adjusted according to the method described above, while the amplitude may be adjusted to maximize an image similarity metric between a feature of the first image and a corresponding feature of the second image. For example, the amplitude may be adjusted by 1) isolating a feature (e.g., droplet) from a first image; and 2) adjusting the amplitude (e.g., of the piezoelectric transducer) to maximize the similarity between the first and second images. This may be completed for a range of different frequencies. In certain embodiments, the first image and the second image appear shifted and the frequency that provides for the lowest shift in the images is chosen as the second frequency when calculating drop delay.

In certain embodiments, the subject methods reduce the need for user input or manual adjustment during setup of a flow cytometer or between analyses of different samples. In some embodiments, methods of interest may partially or fully automate a flow cytometer so that parameters, such as calculation of drop delay, of the flow cytometer are processor controlled. In certain embodiments, methods include determining drop delay of the flow cytometer without any human input. For example, methods may include determining drop delay of the flow stream in the absence of calibration particles (e.g., fluorescent beads). Parameters of the flow cytometer may be adjusted in response to the determined drop delay, such as changing the timing of applying an electrical charge of the flow stream or adjusting the flow rate of the flow stream.

Aspects of the present disclosure also include systems for determining drop delay of a flow stream in a flow cytometer. Systems according to certain embodiments include an imaging sensor configured to capture one or more images of a flow stream that has been subjected to an oscillating vibration in a detection field of a flow cytometer and a processor having memory operably coupled to the processor where the memory includes instructions to obtain a first frequency of drop perturbation of the flow stream, obtain a second frequency of drop perturbation and to determine the drop delay of the flow stream based on the first frequency and the second frequency. For example, the memory may include instructions to obtain the second frequency from a plurality of different drop perturbations, such as instructions to conduct a sweep over a range of frequencies with the oscillating transducer. Systems may be configured to capture one or more images of the flow stream in the detection field at each of the different frequencies. In some embodiments, systems are configured to identify the frequency of the oscillating transducer where the flow stream contains one more distinct drop in the detection field than at the first frequency. In other embodiments, systems are configured to identify the frequency based on maximizing an image similarity metric between a location on a first image and a designated location on a second image. In some embodiments, this location is distinct from the location of break off. In embodiments where the measurement location is offset from the location of droplet breakoff, the determined drop delay is adjusted with a fixed offset term. In some embodiments, images of the flow stream are captured at a moment that is not the instant of droplet breakoff. In those embodiments, the determined drop delay is adjusted with a fixed offset that reflects the difference between the moment of image acquisition and the moment of droplet breakoff. In other embodiments, systems are configured to identify a first frequency and a second frequency of drop perturbation from one or more captured images of a deflected flow stream. For instance, the detection field may be downstream from a deflection plate and the system is configured to determine a first frequency where one or more of the captured images shows a deflection of one or more drops in the detection field and a second frequency where one or more of the captured images exhibits a maximal stream deflection in the detection field.

In some embodiments, the subject systems are configured to determine one or more of the amplitude and phase of drop perturbations in the detection field and include a light source and a sensor (e.g., a position sensing detector such as a sensor having one or more photodiodes, including a quadrant photodiode) for detecting first and second light signals along a vertical axis of the flow stream. In some instances, the light source is a laser. In other instances, the light source is a light emitting diode (LED) or an array of LEDs. In these embodiments, the sensor may be configured to detect forward scattered light from the irradiate flow stream. In certain embodiments, flow cytometers of interest include a flow nozzle having a nozzle chamber and nozzle orifice, a flow channel configured to output the flow stream from the nozzle orifice, an irradiation source that directs a beam of probing light at the flow channel at an interrogation zone and a lens system configured to collect light emitted from the flow stream. In certain embodiments, the flow cytometer includes a flow cell nozzle which is configured to propagate light emitted by a sample in a flow stream upstream through the nozzle orifice by total internal reflectance. The flow cell nozzle, in some instances, includes a nozzle chamber that reflects or transmits light propagated through the nozzle orifice to a light collection system positioned distal from the nozzle orifice.

Aspects of the present disclosure also include a non-transitory computer readable storage medium for determining the drop delay of a flow stream in a flow cytometer. Non-transitory computer readable storage mediums according to certain embodiments include instructions stored thereon having algorithm for obtaining a first frequency of drop perturbation of a flow stream subjected to an oscillating vibration; algorithm for capturing one or more images in a detection field of the flow stream with an imaging sensor; algorithm for obtaining a second frequency of drop perturbation of the flow stream based on one or more of the captured images; and algorithm for determining the drop delay of the flow stream based on the first frequency and the second frequency. In some embodiments, the instructions include an algorithm for obtaining the second frequency from the plurality of different drop perturbation frequencies (e.g., a sweep of frequencies) when one or more of the captured images shows an increase of one distinct drop in the detection field. In other embodiments, the instructions include algorithm for identifying the second frequency based on maximizing an image similarity metric at a designated location in the captured images. In some embodiments, this location is distinct from the location of break off. In embodiments where the measurement location is offset from the location of droplet breakoff, the determined drop delay is adjusted with a fixed offset term. In some embodiments, images of the flow stream are captured at a moment that is not the instant of droplet breakoff. In those embodiments, the determined drop delay is adjusted with a fixed offset that reflects the difference between the moment of image acquisition and the moment of droplet breakoff.

Where the detection field is the flow stream downstream from a deflection plate, instructions may also include algorithm for subjecting the flow stream to an electrical charge upstream from the deflection plate. In these embodiments, the instructions may include obtaining a first frequency when the captured images shows deflection of one or more drops in the detection field and a second frequency when the captured images exhibits a maximal stream deflection in the detection field.

The non-transitory computer readable storage medium may also include instructions for determining amplitude and phase of drop perturbations in the flow stream, such as instructions that include algorithm for irradiating a vertical axis of the flow stream subjected to the oscillating vibration;

algorithm for detecting first and second light signals along the laser irradiated flow stream, such that the first and second light signals are obtained at different positions on a detector; and algorithm for calculating a differential signal between the first signal and second signal. The computer readable storage medium may also include instructions for applying an oscillating vibration to the flow nozzle, such as by a piezoelectric transducer.

BRIEF DESCRIPTION OF THE FIGURES

The invention may be best understood from the following detailed description when read in conjunction with the accompanying drawings. Included in the drawings are the following figures:

FIG. 2A depicts a half-profile image of the flow stream at a first frequency (f1, black line) and an overlayed half-profile image of the flow stream at a second frequency (f2, gray line). FIG. 2B depicts a zoomed-in view of the half-profile image of the first droplet prior to breakoff at the first frequency and the corresponding location in a second image.

FIG. 4 depicts a flow diagram for determining drop delay according to certain embodiments.

DETAILED DESCRIPTION

Figure 1:
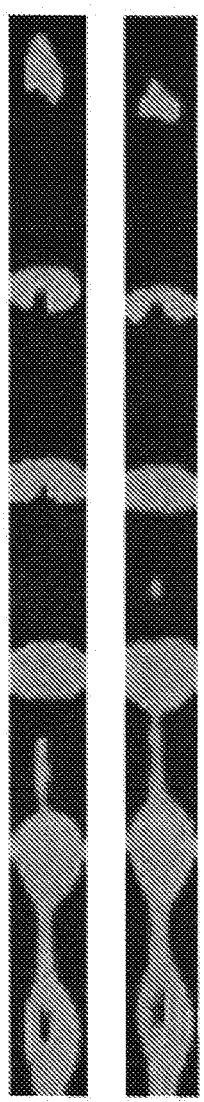
FIG. 1 depicts captured images of a flow stream at the break-off point subjected to an oscillating vibration at two different frequencies according to certain embodiments.

Aspects of the present disclosure include methods and systems for determining drop delay of a flow stream in a flow cytometer. Methods according to certain embodiments include obtaining a first frequency (f1) of drop perturbation of a flow stream subjected to an oscillating vibration, capturing one or more images of the flow stream in a detection field, obtaining a second frequency (f2) of drop perturbation of the flow stream based on one or more of the captured images and determining the drop delay of the flow stream based on the first frequency and the second frequency. Systems for practicing the subject methods having an imaging sensor for capturing one or more images of the flow stream and a processor configured to calculate drop delay using one or more of the captured images are also provided. Non-transitory computer readable storage mediums are also described.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, the present disclosure provides methods for determining drop delay of a flow stream in a flow cytometer. In further describing embodiments of the disclosure, methods for determining drop delay based on a first frequency (f1) and a second frequency (f2) of drop perturbation of the flow stream are first described in greater detail. Next systems having an imaging sensor for capturing one or more images of the flow stream and a processor configured to calculate drop delay using one or more of the captured images are described. Non-transitory computer readable storage mediums are also provided.

Methods for Determining Drop Delay of a Flow Stream in a Flow Cytometer

As summarized above, aspects of the present disclosure include methods for determining drop delay of a flow stream in a flow cytometer. Methods according to certain embodiments include obtaining a first frequency (f1) of drop perturbation of a flow stream subjected to an oscillating vibration, capturing one or more images of the flow stream in a detection field, obtaining a second frequency (f2) of drop perturbation of the flow stream and determining the drop delay of the flow stream based on the first frequency and the second frequency. In embodiments, the subject methods may be fully automated, such as to reduce or entirely eliminate the need for user input or manual determination of drop delay of the flow stream. In certain embodiments, the subject methods eliminate the use of fluorescent particles (e.g., beads) for determining drop delay of a flow cytometer system, such as during setup of the flow cytometer or in between analysis of different samples. In other words, determining the drop delay in certain embodiments may require little to no human intervention or manual input by the user. As discussed in greater detail below, methods may also include adjusting one or more parameters of the flow cytometer using the determined drop delay without any human intervention. For example, the timing of applying an electrical charge to the flow stream or adjusting the flow rate of the flow stream may be adjusted using the determined drop delay.

In practicing methods according to certain embodiments, one or more images of a flow cytometer flow stream are captured in a detection field. By "detection field" is meant the region of the flow stream which is imaged by one or more imaging sensors. In embodiments, methods may include capturing in an image a detection field that spans 0.001 cm or more of the flow stream, such as 0.005 cm or more, such as 0.01 cm or more, such as 0.05 cm or more, such as 0.1 cm or more, such as 0.5 cm or more, such as 1 cm or more, such as 2 cm or more, such as 5 cm or more and including 10 cm or more of the flow stream. The detection field imaged may vary. In embodiments, the detection field is a predetermined length of the flow stream. In some embodiments, the detection field includes the flow stream upstream from the flow stream break-off point and downstream from a sample interrogation point (e.g., laser interrogation point). By "break-off point" is meant the point in the flow stream where the continuous flow stream begins to form discrete droplets. In other embodiments, the detection field includes the flow stream downstream from a deflection plate, where the flow stream is subjected to an electrical charge upstream from the deflection plate. In some examples, the boundaries of the detection field include the flow cell nozzle orifice. In other examples, the boundaries of the detection field include the region where charged particles are deflected by deflector plates during cell sorting. In some embodiments, this location is distinct from the location of break off. In some embodiments, the detection field is offset from the location of droplet breakoff and the determined drop delay is adjusted with a fixed offset term.

In capturing one or more images of the flow stream, a detection field is illuminated with a light source. In some embodiments, the flow stream is illuminated with a broadband light source or with a narrow band of light. Suitable broadband light source protocols may include, but are not limited to a halogen lamp, deuterium arc lamp, xenon arc lamp, stabilized fiber-coupled broadband light source, a broadband LED with continuous spectrum, superluminescent emitting diode, semiconductor light emitting diode, wide spectrum LED white light source, an multi-LED integrated white light source, among other broadband light sources or any combination thereof. Suitable narrow band light sources, include but are not limited to a narrow wavelength LED, laser diode or a broadband light source coupled to one or more optical bandpass filters, diffraction gratings, monochromators or any combination thereof. In certain embodiments, one or more images of the flow stream are captured by illuminating the detection field with an array of infra-red LEDs.

In certain embodiments, the light source is a stroboscopic light source where the flow stream is illuminated with periodic flashes of light. For example, the frequency of light strobe may be 0.01 kHz or greater, such as 0.05 kHz or greater, such as 0.1 kHz or greater, such as 0.5 kHz or greater, such as 1 kHz or greater, such as 2.5 kHz or greater, such as 5 kHz or greater, such as 10 kHz or greater, such as 25 kHz or greater, such as 50 kHz or greater and including 100 kHz or greater. In some instances, the strobe frequency is synchronized with droplet drive frequency. In certain instances, the periodic flashes are confined to a duration much shorter than the duration of one droplet drive cycle. In some instances, the phase of the periodic flashes is distinct from the phase in the drop cycle where droplets break off of the stream. In other instances, the strobe frequency is synchronized with image capture.

Capturing one or more images of the flow stream may include illuminating the flow stream with a combination of light sources, such as with two or more light sources, such as three or more light sources, such as four or more light sources and including five or more light sources. Where more than one light source is employed, the flow stream may be illuminated with the light sources simultaneously or sequentially, or a combination thereof. For example, where images of the flow stream are captured by illuminating with two light sources, the subject methods may include simultaneously illuminating the flow stream with both light sources. In other embodiments, capturing images of the flow stream may include sequentially illuminating with two light sources. Where two light sources are illuminated sequentially, the time each light source illuminates the flow stream may independently be 0.001 seconds or more, such as 0.01 seconds or more, such as 0.1 seconds or more, such as 1 second or more, such as 5 seconds or more, such as 10 seconds or more, such as 30 seconds or more and including 60 seconds or more. In embodiments where images of the flow stream are captured by sequentially illuminating with two or more light sources, the duration the flow stream is illuminated by each light source may be the same or different.

Images of the flow stream may be captured continuously or in discrete intervals. In some instances, methods include capturing images continuously. In other instances, methods include capturing images in discrete intervals, such as capturing an image of the flow stream every 0.001 millisecond, every 0.01 millisecond, every 0.1 millisecond, every 1 millisecond, every 10 milliseconds, every 100 milliseconds and including every 1000 milliseconds, or some other interval.

One or more images may be captured in the detection field, such as 2 or more images of the flow stream in each detection field, such as 3 or more images, such as 4 or more images, such as 5 or more images, such as 10 or more images, such as 15 or more images and including 25 or more images. As described in greater detail below, methods may include obtaining the first frequency and the second frequency of drop perturbation of the flow stream from a plurality of different drop perturbation frequencies, such as by varying the frequency of the oscillating transducer to sweep across a range of different drop perturbation frequencies. In these embodiments, one or more images are captured at each of the different drop perturbation frequencies.

Images of the flow stream in each detection field may be captured at any suitable distance from the flow stream so long as a usable image of the flow stream is captured. For example, images in each detection field may be captured at 0.01 mm or more from the flow stream, such as 0.05 mm or more, such as 0.1 mm or more, such as 0.5 mm or more, such as 1 mm or more, such as 2.5 mm or more, such as 5 mm or more, such as 10 mm or more, such as 15 mm or more, such as 25 mm or more and including 50 mm or more from the flow cytometer flow stream. Images of the flow stream in each detection field may also be captured at any angle from the flow stream. For example, images in each detection field may captured at an angle with respect to the axis of the flow stream which ranges from 10° to 90°, such as from 15° to 85°, such as from 20° to 80°, such as from 25° to 75° and including from 30° to 60°. In certain embodiments, images in each detection field may be captured at a 90° angle with respect to the axis of the flow stream.

In some embodiments, images of the flow stream are captured at a moment that is not the instant of droplet breakoff. As described below, the determined drop delay may be adjusted with a fixed offset that reflects the difference between the moment of image acquisition and the moment of droplet breakoff.

As summarized above, methods include obtaining a first frequency (f1) and a second frequency (f2) of drop perturbations of a flow stream subjected to an oscillating vibration. In some embodiments, methods include where the second frequency is the frequency when images of the flow stream at that frequency contain one more distinct drop in the detection field than at the first frequency. In other embodiments, methods include where the second frequency is the frequency where an image characteristic in the images is most similar in the detection field. The flow stream may be subjected to the oscillating vibration by any convenient protocol. In certain embodiments, the oscillating vibration is applied to the flow nozzle by a transducer, such as by an oscillating piezoelectric transducer.

In some embodiments, the methods include varying the frequency of the oscillating transducer over a plurality of different frequencies and capturing one more images at each of the different frequencies. In some embodiments, the oscillating transducer may be configured to sweep across a range of different drop perturbation frequencies, such as varying the frequency of the oscillating transducer over a plurality of different frequencies in a range from 1000 Hz to 50000 Hz, such as from 1500 Hz to 49500 Hz, such as from 2000 Hz to 49000 Hz, such as from 2500 Hz to 48500 Hz, such as from 5000 Hz to 45000 Hz, such as from 10000 Hz to 42500 Hz, such as from 15000 Hz to 40000 Hz and including varying the frequency of the oscillating transducer over a plurality of different frequencies in a range from 30000 Hz to 35000 Hz. In some embodiments, the oscillating transducer is configured to apply a series of incrementally increasing frequencies to the flow nozzle. For instance, methods may including sweeping across a range of oscillating frequencies by serially increasing the transducer frequency by 0.01 Hz or more, such as by 0.05 Hz or more, such as by 0.1 Hz or more, such as by 0.5 Hz or more, such as by 1 Hz or more, such as by 2 Hz or more, such as by 5 Hz or more, such as by 10 Hz or more, such as by 25 Hz or more, such as by 50 Hz or more, such as by 75 Hz or more and including by 100 Hz or more. In one example, the oscillating frequency of the transducer is varied at increments of 1 Hz or more (e.g., 10 Hz or more) over a range from 1000 Hz to 10000 Hz, such as from 1500 Hz to 9000 Hz, such as from 2000 Hz to 8000 Hz, such as from 3000 Hz to 7000 Hz and including at increments of 1 Hz or more (e.g., 10 Hz or more) over a range from 4000 Hz to 6000 Hz.

In another example, the oscillating frequency of the transducer is varied over a range at increments of 1 Hz or more (e.g., 10 Hz or more) from 10000 Hz to 20000 Hz, such as from 11000 Hz to 19000 Hz, such as from 12000 Hz to 18000 Hz, such as from 13000 Hz to 17000 Hz, and including at increments of 1 Hz or more (e.g., 10 Hz or more) from 14000 Hz to 16000 Hz. In yet another example, the oscillating frequency of the transducer is varied over a range at increments of 1 Hz or more (e.g., 10 Hz or more) from 20000 Hz to 30000 Hz, such as from 21000 Hz to 29000 Hz, such as from 22000 Hz to 28000 Hz, such as from 23000 Hz to 27000 Hz, and including at increments of 1 Hz or more (e.g., 10 Hz or more) from 24000 Hz to 26000 Hz. In still other examples, the oscillating frequency of the transducer is varied over a range at increments of 1 Hz or more (e.g., 10 Hz or more) from 30000 Hz to 35000 Hz, such as from 30500 Hz to 34000 Hz, such as from 31000 Hz to 33500 Hz and including at increments of 1 Hz or more (e.g., 10 Hz or more) from 30000 Hz to 32000 Hz.

Any number of different oscillating frequencies may be applied by the transducer during frequency sweeping, such as applying 5 or more different oscillating frequencies, such as 10 or more, such as 15 or more, such as 20 or more, such as 25 or more, such as 30 or more and including applying 50 or more different oscillating frequencies during frequency sweeping. In some embodiments of the present disclosure, the second frequency is obtained when one or more of the captured images show an increase of one integer drop in the detection field. In other words, the second frequency is the applied frequency of the oscillating transducer when the captured images at that frequency show one additional distinct drop in the flow stream in the detection field. Determining from the captured images when the flow stream includes one additional distinct drop may be determined manually, such as by a user viewing each captured image or may be processor controlled (as described below) where the processor includes algorithm for assessing each of the captured images to determine that one additional drop is present in the flow stream in the detection field.

In other embodiments of the present disclosure, the second frequency is obtained by comparing the similarity of a feature in the captured images, such as a droplet present in the first image with a designated location on the second image using a metric such as cross-correlation. The feature may be any convenient characteristic in the captured image and may be a droplet, the flow stream or other feature (e.g., noise characteristic). In some embodiments, the image feature is a profile of the flow stream. In other embodiments, the image feature is a profile of a droplet. In yet other embodiments, the image feature is a plurality of droplets at or near the break-off point of the flow stream. In certain embodiments, methods include comparing half-profile images of the flow stream (e.g., overlaying the images) and determining similarity between the half-profile images of the flow stream. In these embodiments, comparing may include comparing the amplitude or the spatial characteristics of the flow stream. In certain instances, methods include comparing the similarity between the height of the peaks of the half-profile image. In other instances, methods include comparing the similarity in the spatial similarity between the peaks of the half-profile image. The similarity between the image feature in the captured image at the first frequency and the image feature in the captured image at the second frequency may be 10% or greater, such as 15% or greater, such as 20% or greater, such as 25% or greater, such as 50% or greater, such as 60% or greater, such as 70% or greater, such as 75% or more greater, such as 80% or greater, such as 85% or greater, such as 90% greater, such as 95% or greater, such as 99% or greater.

In certain embodiments, the image similarity is determined by a minimal spatial shift of an image characteristic from the image at the first frequency and the image at the second frequency. In these embodiments, the spatial shift in images determined to have a minimal spatial shift may be 25% or less, such as 20% or less, such as 15% or less, such as 10% or less, such as 5% or less, such as 4% or less, such as 3% or less, such as 2% or less, such as 1% or less, such as 0.5% or less, such as 0.1% or less, such as 0.05% or less, such as 0.01% or less, such as 0.005% or less and including 0.001% or less. In certain embodiments, the image characteristic is determined to exhibit the minimal spatial shift when the image characteristic is identical (i.e., zero spatial shift) in the first image (captured image at the first frequency) to the second image (captured image at the second frequency).

Determining from the captured images where an image feature is most similar may be determined manually, such as by a user viewing each captured image or may be processor controlled (as described below) where the processor includes algorithm for assessing each of the captured images to determine that the image characteristic is most similar in the detection field. The second frequency is the applied frequency of the oscillating transducer when the when the metric is maximized.

Figure 2A:
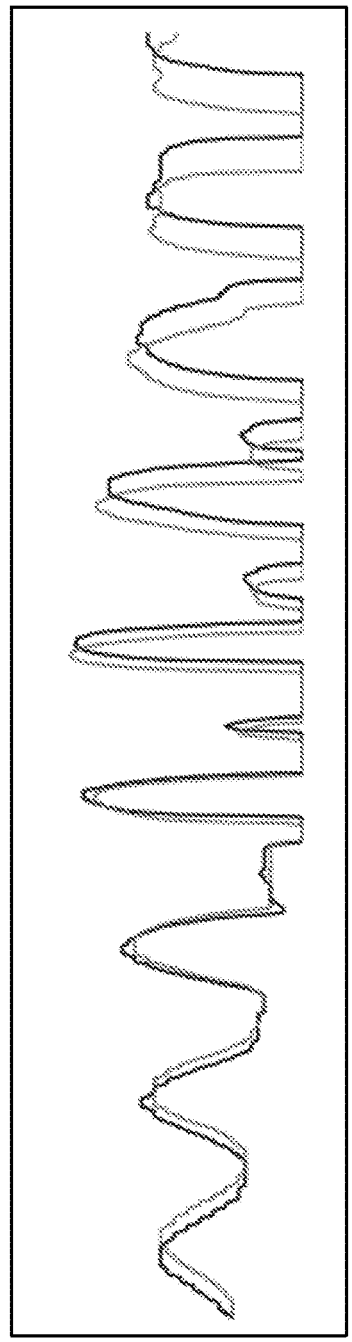
FIGS. 2A-2B depicts obtaining a first frequency (f1) and a second frequency (f2) of drop perturbations of a flow stream subjected to a oscillating vibration according to another embodiment of the present disclosure.
Figure 2B:
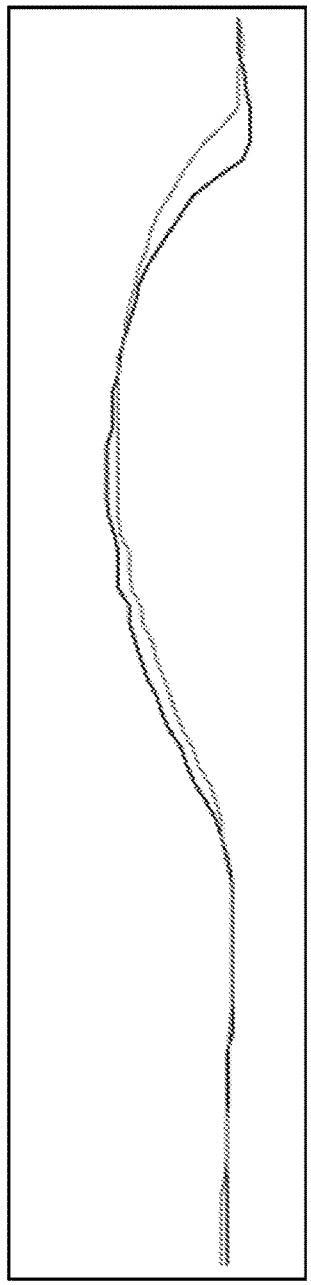

FIG. 1 illustrates obtaining a first frequency (f1) and a second frequency (f2) of drop perturbations of a flow stream subjected to an oscillating vibration according to certain embodiments of the present disclosure. FIG. 1 depicts captured images at the break-off point of the flow stream subjected to an oscillating vibration at two different frequencies. As shown in FIG. 1, the captured image at the second frequency (f2) shows a flow stream that contains one more distinct drop in the detection field than at the first frequency. Drop delay for this flow stream can be calculated (as described below) based on the first frequency (f1) and the second frequency (f2). FIGS. 2A-2B depicts obtaining a first frequency (f1) and a second frequency (f2) of drop perturbations of a flow stream subjected to a oscillating vibration according to another embodiment of the present disclosure. FIG. 2A depicts a half-profile image of the flow stream at a first frequency (f1, black line) and an overlayed half-profile image of the flow stream at a second frequency (f2, gray line). Drop delay for this flow stream can be determined based on the overlayed half-profile image of the second image of the flow stream that gives the lowest deviation between that of the first image. In certain instances, the frequency which gives an overlayed half-profile image that is most similar (e.g., most spatially similar) to that of the first image is identified as the second frequency. FIG. 2B depicts a zoomed-in view of the half-profile image of the first droplet prior to breakoff at the first frequency and the corresponding location in a second image. Differences in feature similarity can be, in certain embodiments, corrected by adjusting amplitude. In some embodiments, to evaluate the similarity between the overlayed half-profile images (e.g., spatially similarity), the amplitude is first corrected (e.g., normalized with respect to each other).

In some embodiments, applying a plurality of different frequencies to obtain the first frequency and the second frequency includes applying a series of 5 incrementally increasing oscillating frequencies: $a_1$, $a_2$, $a_3$, $a_4$, and $a_5$. In these embodiments, the first frequency (f1) is $a_1$ and the second frequency is the frequency ($a_2$, $a_3$, $a_4$, or $a_5$) where one or more the captured images show an increase of one integer drop in the flow stream in the detection field. For instance, when one or more of the captured images show an increase of one integer drop in the detection field at frequency $a_4$, the frequency $a_4$ is determined to be the second frequency, f2. To illustrate, in one example, a series of 5 different frequencies ranging from 30000 Hz to 32000 Hz may be applied by an oscillating transducer (e.g., $a_1$=30000 Hz; $a_2$=30500 Hz; $a_3$=31000 Hz, $a_4$=31500 Hz and $a_5$=32000 Hz) Where one or more of the captured images show an increase of one integer drop in the detection field at frequency of 31000 Hz, the first frequency and the second frequency obtained according to the subject methods are 30000 Hz (first frequency) and 31000 Hz (second frequency).

In other embodiments, applying a plurality of different frequencies to obtain the first frequency and the second frequency includes applying a series of 5 incrementally increasing oscillating frequencies: $a_1$, $a_2$, $a_3$, $a_4$, and $a_5$. In these embodiments, the first frequency (f1) is $a_1$ and the second frequency is the frequency ($a_2$, $a_3$, $a_4$, or $a_5$) where one or more the captured images show the maximal similarity of an image feature to that in f1 in the flow stream in the detection field. For instance, when the captured images show a maximal similarity of an image feature to that in f1 in the flow stream in the detection field at frequency $a_4$, the frequency $a_4$ is determined to be the second frequency, f2. To illustrate, in one example, a series of 5 different frequencies ranging from 30000 Hz to 32000 Hz may be applied by an oscillating transducer (e.g., $a_1$=30000 Hz; $a_2$=30500 Hz; $a_3$=31000 Hz, $a_4$=31500 Hz and $a_5$=32000 Hz) Where one or more of the captured images show a maximal similarity of an image feature to that of f1 in the flow stream in the detection field at frequency of 31000 Hz, the first frequency and the second frequency obtained according to the subject methods are 30000 Hz (first frequency) and 31000 Hz (second frequency). For example, where one or more of the captured images show a minimal spatial shift of an image feature to that of f1 in the flow stream in the detection field at frequency of 31000 Hz, the first frequency and the second frequency obtained according to the subject methods are 30000 Hz (first frequency) and 31000 Hz (second frequency).

In yet other embodiments, applying a plurality of different frequencies to obtain the first frequency and the second frequency includes applying a series of 10 incrementally increasing oscillating frequencies: $a_1$, $a_2$, $a_3$, $a_4$, $a_5$, $a_6$, $a_7$, $a_8$, $a_9$, and $a_{10}$. In these embodiments, the first frequency (f1) according to the subject methods is $a_1$ and the second frequency is the frequency ($a_2$, $a_3$, $a_4$, $a_5$, $a_6$, $a_7$, $a_8$, $a_9$, or $a_{10}$) where one or more the captured images show an increase of one integer drop in the detection field. For instance, when one or more of the captured images show an increase of one integer drop in the detection field at frequency $a_7$, the frequency $a_7$ is determined as the second frequency, f2. To illustrate, in one example, a series of 10 different frequencies ranging from 30000 Hz to 32000 Hz may be applied by an oscillating transducer (e.g., $a_1$=30000 Hz; $a_2$=30500 Hz; $a_3$=31000 Hz, $a_4$=31100 Hz; $a_5$=31200 Hz; $a_6$=31300; $a_7$=31400; $a_8$=31500; $a_9$=31550; and $a_{10}$=31800) Where one or more of the captured images show an increase of one integer drop in the detection field at frequency of 31500 Hz, the first frequency and the second frequency obtained according to embodiments of the disclosure are 30000 Hz (first frequency, f1) and 31500 Hz (second frequency, f2).

In still other embodiments, applying a plurality of different frequencies to obtain the first frequency and the second frequency includes applying a series of 10 incrementally increasing oscillating frequencies: $a_1, a_2, a_3, a_4, a_5, a_6, a_7, a_8, a_9$, and $a_{10}$. In these embodiments, the first frequency (f1) according to the subject methods is $a_1$ and the second frequency is the frequency ($a_2, a_3, a_4, a_5, a_6, a_7, a_8, a_9$, or $a_{10}$) where one or more the captured images show the maximal similarity of an image feature to that in f1 in the flow stream in the detection field. For instance, when one or more of the captured images show a maximal similarity of an image feature to that in f1 in the flow stream in the detection field at frequency $a_7$, the frequency $a_7$ is determined as the second frequency, f2. To illustrate, in one example, a series of 10 different frequencies ranging from 30000 Hz to 32000 Hz may be applied by an oscillating transducer (e.g., $a_1$=30000 Hz; $a_2$=30500 Hz; $a_3$=31000 Hz, $a_4$=31100 Hz; $a_5$=31200 Hz; $a_6$=31300; $a_7$=31400; $a_8$=31500; $a_9$=31550; and $a_{10}$=31800) Where one or more of the captured images show a maximal similarity of an image feature (e.g., spatial similarity) to that in f1 in the flow stream in the detection field at frequency of 31500 Hz, the first frequency and the second frequency obtained according to embodiments of the disclosure are 30000 Hz (first frequency, f1) and 31500 Hz (second frequency, f2). For example, where one or more of the captured images shows a minimal spatial shift of an image feature to that in f1 in the flow stream in the detection field at frequency of 31500 Hz, the first frequency and the second frequency obtained according to embodiments of the disclosure are 30000 Hz (first frequency, f1) and 31500 Hz (second frequency, f2).

In certain embodiments, the detection field is downstream from a deflection plate and the flow stream is further subjected to an electrical charge upstream from the deflection plate such that the first frequency and second frequency are determined from one or more captured images of a deflected flow stream. In these embodiments, the first frequency is the applied frequency of the oscillating transducer when one or more of the captured images begins to show a deflection of flow stream drops in the detection field. As discussed above, the second frequency may be obtained by varying the frequency of the oscillating transducer over a plurality of different frequencies, such as by sweeping across a range of different drop perturbation frequencies. Any number of different frequencies may be applied by the oscillating transducer during frequency sweeping, such as applying 5 or more different frequencies, such as 10 or more, such as 15 or more, such as 20 or more, such as 25 or more, such as 30 or more and including applying 50 or more different frequencies with the oscillating transducer during frequency sweeping. In some embodiments, the oscillating transducer may be configured to sweep across a range of different drop perturbation frequencies, such as varying the frequency of the oscillating transducer over a plurality of different frequencies in a range from 1000 Hz to 50000 Hz, such as from 1500 Hz to 49500 Hz, such as from 2000 Hz to 49000 Hz, such as from 2500 Hz to 48500 Hz, such as from 5000 Hz to 45000 Hz, such as from 10000 Hz to 42500 Hz, such as from 15000 Hz to 40000 Hz and including varying the frequency of the oscillating transducer over a plurality of different frequencies in a range from 30000 Hz to 35000 Hz.

For instance, methods may including sweeping across a range of frequencies by varying the oscillating transducer drive frequency by 10 Hz or more, such as by 25 Hz or more, such as by 50 Hz or more, such as by 75 Hz or more, such as by 100 Hz or more, such as by 125 Hz or more, such as by 150 Hz or more, such as by 200 Hz or more, such as by 300 Hz or more and including by 1000 Hz or more. In one example, the oscillating frequency of the transducer is varied over a range from 1000 Hz to 10000 Hz, such as from 1500 Hz to 9000 Hz, such as from 2000 Hz to 8000 Hz, such as from 3000 Hz to 7000 Hz and including over a range from 4000 Hz to 6000 Hz. In another example, the oscillating frequency of the transducer is varied over a range from 10000 Hz to 20000 Hz, such as from 11000 Hz to 19000 Hz, such as from 12000 Hz to 18000 Hz, such as from 13000 Hz to 17000 Hz, and including from 14000 Hz to 16000 Hz. In yet another example, the oscillating frequency of the transducer is varied over a range from 20000 Hz to 30000 Hz, such as from 21000 Hz to 29000 Hz, such as from 22000 Hz to 28000 Hz, such as from 23000 Hz to 27000 Hz, and including from 24000 Hz to 26000 Hz. In still other examples, the oscillating frequency of the transducer is varied over a range from 30000 Hz to 35000 Hz, such as from 30500 Hz to 34000 Hz, such as from 31000 Hz to 33500 Hz and including from 30000 Hz to 32000 Hz.

In these embodiments, the first frequency is determined to be the frequency applied by the oscillating transducer when one or more of the captured images begins to show a deflection of flow stream drops in the detection field and the second frequency is determined to be the frequency applied by the oscillating transducer that results in a maximal stream deflection by the deflection plate in the detection field. Determining from the captured images when the flow stream exhibits maximal stream deflection by the deflection plate may be determined manually, such as by a user viewing each captured image or may be computer controlled where a processor having algorithm for assessing each of the captured images is configured to determine a maximal stream deflection of the flow stream from the captured images at the plurality of applied frequencies.

Figure 3A:
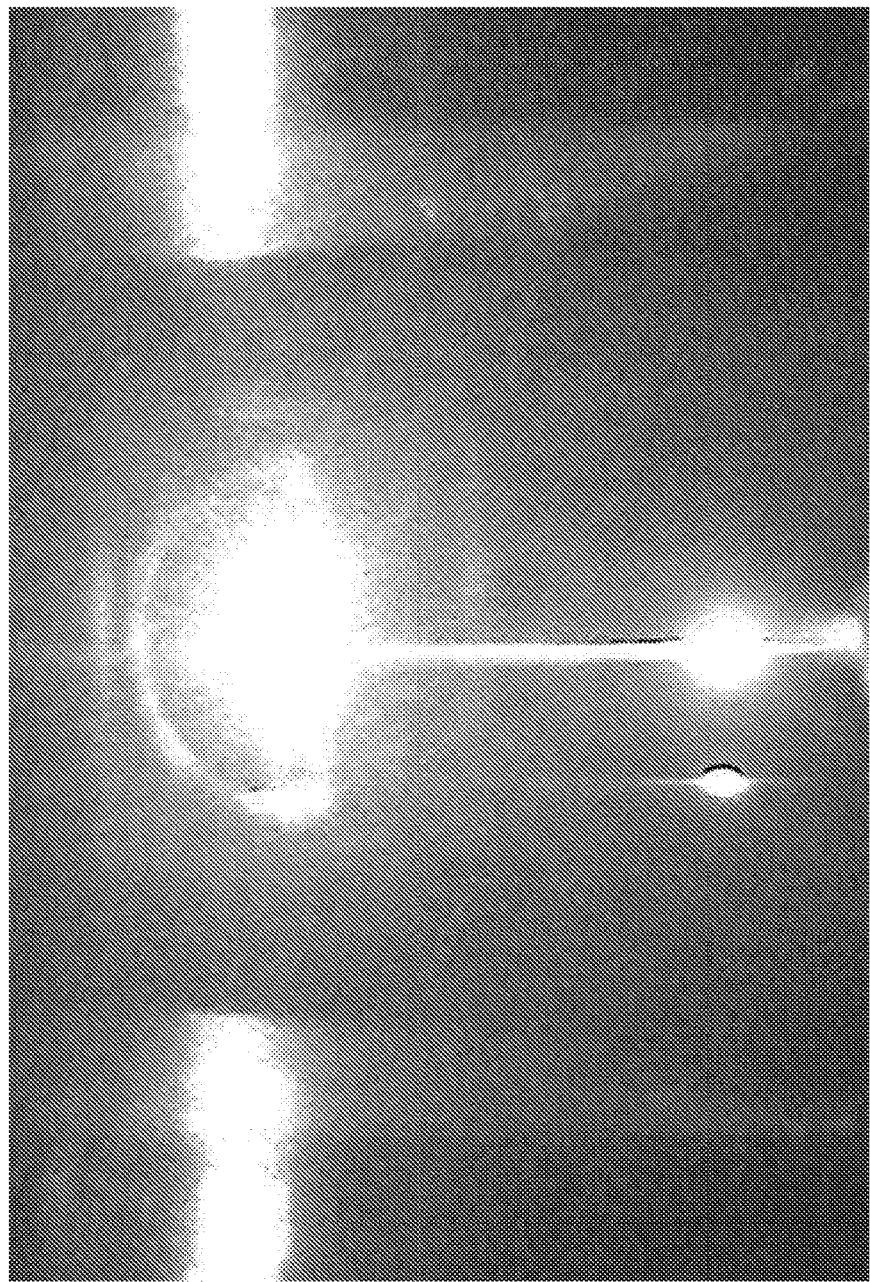
FIG. 3A depicts an image of a flow stream deflected by a deflection plate at a first frequency of drop perturbation according to certain embodiments.
Figure 3B:
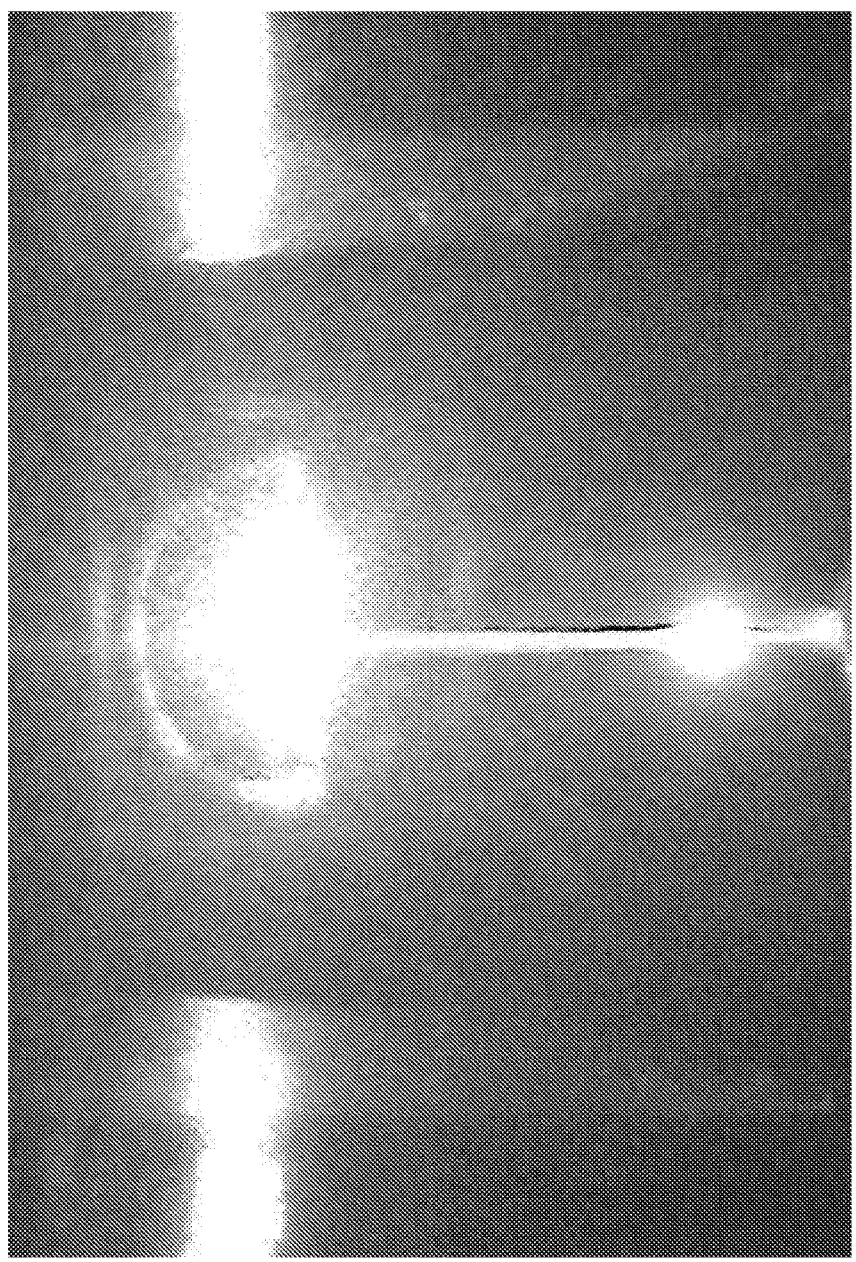
FIG. 3B depicts an image of a flow stream that is not deflected by a deflection plate during a sweep over a range of oscillating frequencies according to certain embodiments.

FIG. 3A depicts a captured image showing deflection of a flow stream according to certain embodiments. As depicted in FIG. 3A, droplets are deflected at an applied oscillating frequency which is designated as the first frequency (f1) during a sweep over a range of oscillating frequency. As discussed above, a second frequency is obtained where the captured images during a frequency sweep depict a maximal stream deflection. During sweeps across a range of applied oscillating frequencies, captured images obtained at frequencies between the first frequency and second frequency (i.e., greater frequency than f1, but less than f2) will exhibit no deflection by the deflection plates, which is depicted by the captured image of the flow stream in FIG. 3B.

In certain embodiments, determining the second frequency where a flow stream exhibits a maximal stream deflection includes adjusting the drop charge voltage (e.g., to give a larger and more easily discernible flow stream deflection in the captured images). For example, in some instances, the drop charging voltage is increased such as by 0.01 V or more, such as 0.05 V or more, such as 0.1 V or more, such as by 0.5V or more, such as by 1V or more, such as by 5V or more, such as by 10V or more, such as by 15V or more, such as by 25V or more, such as by 50V or more and including increasing the drop charging voltage by 75V or more. For example, the drop charging voltage may be increased by 1% or more, such as by 5% or more, such as by 10% or more, such as by 15% or more, such as by 25% or more, such as by 50% or more, such as by 75% or more and including increasing the drop charging voltage by 90% or more. In other instances, determining the second frequency where a flow stream exhibits a maximal stream deflection includes reducing the drop charging voltage, such as by 0.01 V or more, such as 0.05 V or more, such as 0.1

V or more, such as by 0.5V or more, such as by 1V or more, such as by 5V or more, such as by 10V or more, such as by 15V or more, such as by 25V or more, such as by 50V or more and including reducing the drop charging voltage by 75V or more. For example, the drop charging voltage may be reduced by 1% or more, such as by 5% or more, such as by 10% or more, such as by 15% or more, such as by 25% or more, such as by 50% or more, such as by 75% or more and including reducing the drop charging voltage by 90% or more.

In embodiments of the present disclosure, the first frequency and the second frequency are determined using the captured images and are not determined based on a detection of current from the charged flow stream drops.

As summarized above, the drop delay of the flow stream is determined based on the obtained first frequency (f1) and second frequency (f2). In certain embodiments, drop delay is calculated according to Formula 1:

$$\text{Drop Delay} = [f1/(f2-f1)] \qquad \text{Formula 1}$$

where drop delay is expressed as the number of drop periods in the detection field (e.g., a detection field that includes the flow stream upstream from the flow stream break-off point and downstream from the laser interrogation point or a detection field that includes a deflected flow stream downstream from a deflection plate)

In other embodiments, the similarity feature at f1 is not the drop breakoff point and the image may be acquired at a time in the drop breakoff cycle that is not the moment of breakoff. In these embodiments, drop delay is calculated according to Formula 2:

$$\text{Drop Delay} = [f1/(f2-f1)] + o1 + o2 \qquad \text{Formula 2}$$

where terms have the meanings described in Formula 1, together with two introduced offset terms o1 and o2. o1 refers to the offset in drop delay introduced by use of a similarity feature that is not the drop breakoff point. o2 refers to the offset in drop delay introduced by acquiring the first and second images at a time that is not the moment of breakoff.

In some embodiments, methods include maintaining constant one or more of the amplitude and phase of drop perturbations at each of the plurality of frequencies during frequency sweeping. In other words, one or more of the amplitude and phase of drop perturbations are adjusted to be equal at each of the different frequencies applied by the oscillating transducer. Accordingly, in embodiments the amplitude and/or phase at each of the different applied frequencies is equal to the amplitude and/or the phase of the first frequency.

In some embodiments, methods include maximizing the similarity of some image feature at each of the plurality of frequencies during frequency sweeping. In other words, the amplitude of drop perturbations are adjusted at each of the different frequencies applied by the oscillating transducer to maximize image similarity between corresponding image features at f1 and f2.

To adjust the amplitude and phase at each of the different applied drop perturbation frequencies, the subject methods may also include determining the amplitude and phase of drop perturbations at each of the different frequencies and adjusting the amplitude and phase of the oscillating transducer. In certain embodiments, light is irradiated onto the flow stream and is refracted by the drop perturbations in the flow stream onto a detector. In these embodiments, the perturbations may refract light in an upward direction to a detector at a first time period and refract light in a downward direction to the detector at a second time period. The difference between the amplitude of the light signal from the upward refracted light and the downward refracted light may be calculated giving a differential signal. The amplitude and phase of drop perturbations at each of the different frequencies may be determined using the differential signal.

The flow stream may be irradiated at any suitable vertical position along the flow stream so long as light signals from scattered light by the flow stream are sufficiently detected. In certain embodiments, the light source is a laser configured to irradiate the flow stream in the detection field, such as in the flow stream upstream from the flow stream break-off point and downstream from the flow cell nozzle orifice or in the flow stream downstream from a deflection plate. In other embodiments, the flow stream is irradiated at a position immediately adjacent to the flow cell nozzle orifice. In other embodiments, the flow stream is irradiated at a position downstream from the flow cell nozzle orifice, such as at a position 0.001 mm from the flow cell nozzle orifice, such as 0.005 mm or more, such as 0.01 mm or more, such as 0.05 mm or more, such as 0.1 mm or more, such as 0.5 mm or more, such as 1 mm or more, such as 2 mm or more, such as 5 mm or more and including 10 mm or more downstream from the flow cell nozzle orifice. The flow stream may be irradiated at one or more vertical positions, such as at 2 or more, such as at 3 or more, such as at 4 or more, such as at 5 or more and including irradiating the flow stream at 10 or more vertical positions.

The wavelength of light used to determine amplitude and phase of drop perturbations in the flow stream may vary, ranging from 200 nm to 1500 nm, such as from 250 nm to 1250 nm, such as from 300 nm to 1000 nm, such as from 350 nm to 900 nm and including from 400 nm to 800 nm. For example, the light source may include a broadband light source emitting light having wavelengths from 200 nm to 900 nm. In other instances, the light source includes a narrow band light source emitting a wavelength ranging from 200 nm to 900 nm. For example, the light source may be a narrow band LED (1 nm-25 nm) emitting light having a wavelength ranging between 200 nm to 900 nm. In some embodiments, the light source is a laser, such as continuous wave laser. For example, the laser may be a diode laser, such as an ultraviolet diode laser, a visible diode laser and a near-infrared diode laser. In some instances, the diode laser outputs light at wavelengths ranging from 375 nm to 1000 nm, such as from 405 nm to 875 nm, such as from 450 nm to 800 nm, such as from 500 nm to 650 nm and including from 525 nm to 625 nm.

The flow stream may be irradiated by the light source at any suitable distance from the flow stream, such as at a distance of 0.001 mm or more from the flow stream, such as 0.005 mm or more, such as 0.01 mm or more, such as 0.05 mm or more, such as 0.1 mm or more, such as 0.5 mm or more, such as 1 mm or more, such as 5 mm or more, such as 10 mm or more, such as 25 mm or more and including at a distance of 100 mm or more from the flow stream. Likewise, the flow stream may be irradiated by the light source at any suitable angle with respect to the vertical axis of the flow stream (i.e., the angle the beam of irradiation makes with the vertical axis of the flow stream), such as at an angle ranging from 10° to 90°, such as from 15° to 85°, such as from 20° to 80°, such as from 25° to 75° and including from 30° to 60°. In certain embodiments, the flow stream is irradiated by the light source at a 90° angle with respect to the vertical axis of the flow stream (i.e., irradiation by the light source is orthogonal to the vertical axis of the flow stream)

In assessing amplitude and phase of drop perturbations in the flow stream, the flow stream may be irradiated continuously or in discrete intervals. In some instances, methods include irradiating the flow stream with the light source continuously, such as where amplitude and phase of drop perturbations in the flow stream is monitored by collecting real-time data. In other instances, methods include irradiating the flow stream with the light source in discrete intervals, such as irradiating the flow stream every 0.001 milliseconds, every 0.01 milliseconds, every 0.1 milliseconds, every 1 millisecond, every 10 milliseconds, every 100 milliseconds and including every 1000 milliseconds, or some other interval. Where the flow stream is irradiated at discrete intervals, the frequency of irradiation may depend such as on the concentration of components in the flow stream (e.g., cells) as well as the flow rate of the flow stream.

To determine the amplitude and phase of the drop perturbations at each of the plurality of frequencies applied by the oscillating transducer, first and second light signals are detected along a vertical axis of the irradiated flow stream. The light signals may be detected at any suitable distance from the flow stream so long as a usable light signal is detected. For example, the light signals may detected at 0.01 mm or more from the flow stream, such as 0.05 mm or more, such as 0.1 mm or more, such as 0.5 mm or more, such as 1 mm or more, such as 2.5 mm or more, such as 5 mm or more, such as 10 mm or more, such as 15 mm or more, such as 25 mm or more and including 50 mm or more from the flow stream. The light signals may also be detected at any angle from the flow stream. For example, light signals may be detected at an angle with respect to the vertical axis of the flow stream which ranges from 10° to 90°, such as from 15° to 85°, such as from 20° to 80°, such as from 25° to 75° and including from 30° to 60°. In some instances, detectors (as described in greater detail below) are positioned at 30° to 60° with respect to the vertical axis of the flow stream.

One or more light signals may be detected at each position irradiated along the flow stream by the light source, as described above. For example, two or more light signals, such as three or more light signals, such as four or more light signals, such as five or more light signals and including 10 or more light signals may be detected at each position irradiated along the flow stream by the light source. Where irradiation is continuous, one or more light signals may be detected at different times while irradiating the flow stream, such as two or more light signals, such as three or more light signals, such as four or more light signals, such as five or more light signals and including 10 or more light signals may be detected at different times while irradiating the flow stream.

In certain embodiments, light signals from the irradiated flow stream are from light detected by one or more stationary detectors positioned adjacent to the flow stream in a forward configuration from the light source. For example, the light signals from the irradiated flow stream may be detected by one or more detectors configured as forward scatter detectors. In some embodiments, detecting first and second light signals from the irradiated flow stream includes moving the light source and one or more detectors alongside the path of the flow stream in the detection field, such as moving the light source and detectors upstream or downstream alongside the flow stream detecting first and second light signals at a plurality of the positions along the vertical axis of the flow stream in the detection field. For example, a first and second light may be detected at one or more vertical positions along the flow stream, such as at 2 or more positions, such as at 3 or more positions, such as at 5 or more positions and including at 10 or more vertical positions along the flow stream. Where the light signals are collected at more than one vertical position along the flow stream in the detection field, the distance between each position along the flow stream may vary, such as being separated by 0.001 mm or more, such as by 0.005 mm or more, such as by 0.01 mm or more, such as by 0.05 mm or more, such as by 0.1 mm or more, such as by 0.5 mm or more, such as by 1 mm or more, such as by 5 mm or more, such as by 10 mm or more, such as by 25 mm or more and including detecting light signals at two or more vertical positions that are separated by 100 mm or more.

The light signals may be detected by any convenient positional sensing detecting protocol, including but not limited to photosensors or photodetectors, such as active-pixel sensors (APSs), quadrant photodiodes, wedge detectors image sensors, charge-coupled devices (CCDs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In one embodiment, the light signals are detected with a quadrant photodiode, e.g., as described in U.S. Provisional Patent Application No. 62/091,421; the disclosure of which is herein incorporated by reference. In another embodiment, the light signals are detected with a wedge detector, e.g., as described in U.S. Pat. Nos. 7,362,424 and 7,679,039; the disclosures of which are herein incorporated by reference. The active detecting surface area of each region of the position sensing detector (e.g., quadrant photodiode) may vary, such as from $0.01\ cm^2$ to $10\ cm^2$, such as from $0.05\ cm^2$ to $9\ cm^2$, such as from $0.1\ cm^2$ to $8\ cm^2$, such as from $0.5\ cm^2$ to $7\ cm^2$ and including from $1\ cm^2$ to $5\ cm^2$.

The amplitude and phase of the drop perturbations at each of the plurality of frequencies applied by the oscillating transducer are assessed based on the calculated differential signal between the first and second light signals. In certain embodiments, amplitude and phase of the drop perturbations at each of the plurality of frequencies are adjusted in response to the assessed amplitude and phase. For example, the amplitude and phase of drop perturbations may be maintained constant at each applied frequency by adjusting the amplitude and phase of the oscillating transducer. In some embodiments, adjusting the amplitude and phase includes increasing the amplitude of the oscillating transducer, such as by increasing the amplitude by 1% or more, such as by 5% or more, such as by 10% or more, such as by 25% or more, such as by 50% or more and including by 2-fold or more, such as 3-fold or more, such as 4-fold or more and including by increasing the amplitude of the oscillating transducer by 5-fold or more. In other embodiments, adjusting the amplitude and phase includes decreasing the amplitude of the oscillating transducer, such as by decreasing the amplitude by 1% or more, such as by 5% or more, such as by 10% or more, such as by 25% or more, such as by 50% or more and including by 2-fold or more, such as 3-fold or more, such as 4-fold or more and including by the amplitude of the oscillating transducer by 5-fold or more. In other embodiments, adjusting the amplitude and phase includes introducing a full or partial phase shift to the phase of the drop perturbations determined from the differential signal. For example, methods may include introducing a phase shift of $\pi/64$ or more, such as a phase shift of $\pi/32$, such as a phase shift of $\pi/16$, such as a phase shift of $\pi/8$, such as a phase shift of $\pi/4$, such as a phase shift of $\pi/2$ and including a full phase shift of π to the phase of the drop perturbations determined from the differential signal.

In certain embodiments, methods include assessing amplitude and phase of the drop perturbations and automatically adjusting one or both of amplitude and phase of the oscillating transducer so that the amplitude and phase of drop perturbations at each of the plurality of frequencies is maintained constant. In other words, methods include providing feedback based on monitoring the amplitude and phase of drop perturbations of the flow stream at each frequency and automatically making one or more adjustments to the oscillating transducer. By "automatic" is meant that adjustments to the amplitude and phase of the oscillating transducer made in response to the assessed amplitude and phase requires little to no human intervention or manual input. In certain embodiments, the amplitude of the oscillating transducer is adjusted in accordance with the subject methods without any human intervention. In other embodiments, the phase of the oscillating transducer is adjusted in accordance with the subject methods without any human intervention.

As summarized above, the subject methods may also include adjusting one or more parameters of the flow cytometer using the determined drop delay without any human intervention. In some embodiments, the timing of applying an electrical charge to a flow stream may be adjusted in response to the determined drop delay. For example, in some instances the application of an electrical charge to a flow stream may be delayed by 0.001 milliseconds or more, such as by 0.005 milliseconds or more, such as by 0.01 milliseconds or more, such as by 0.05 milliseconds or more, such as by 0.1 milliseconds or more, such as by 0.5 milliseconds or more, such as by 1 millisecond or more, such as by 5 milliseconds or more, such as by 10 milliseconds or more, such as by 100 milliseconds or more and including delaying the application of an electrical charge to the flow stream by 500 milliseconds or more.

In still other embodiments, the flow rate of the flow stream may be adjusted using the determined drop delay. In some instances, the flow rate of the flow stream may be increased in response to the determined drop delay, such as by increasing the flow rate of the flow stream by 0.1 μL/min or more, such as by 0.5 μL/min or more, such as by 1 μL/min or more, such as by 5 μL/min or more, such as by 10 μL/min or more, such as by 25 μL/min or more, such as by 50 μL/min or more, such as by 100 μL/min or more, such as by 250 μL/min or more and including by 500 μL/min or more. For example, the flow rate of the flow stream may be increased by 1% or more in response to the determined drop delay, such as by 5% or more, such as by 10% or more, such as by 15% or more, such as by 25% or more, such as by 50% or more, such as by 75% or more and including increasing the flow rate of the flow stream by 90% or more. In other instances, the flow rate of the flow stream may be decreased in response to the determined drop delay, such as by decreasing the flow rate by by 0.1 μL/min or more, such as by 0.5 μL/min or more, such as by 1 μL/min or more, such as by 5 μL/min or more, such as by 10 μL/min or more, such as by 25 μL/min or more, such as by 50 μL/min or more, such as by 100 μL/min or more, such as by 250 μL/min or more and including by 500 μL/min or more. For example, the flow rate of the flow stream may be decreased by 1% or more in response to the determined drop delay, such as by 5% or more, such as by 10% or more, such as by 15% or more, such as by 25% or more, such as by 50% or more, such as by 75% or more and including increasing the flow rate of the flow stream by 90% or more.

Systems for Determining Drop Delay of a Flow Stream in a Flow Cytometer

Aspects of the present disclosure also include systems for determining drop delay of a flow stream in a flow cytometer. Systems according to certain embodiments include an imaging sensor configured to capture one or more images of a flow stream that has been subjected to an oscillating vibration in a detection field of a flow cytometer and a processor having memory operably coupled to the processor where the memory includes instructions to obtain a first frequency (f1) of drop perturbation of the flow stream, obtain a second frequency (f2) of drop perturbation based on one or more of the captured images and to determine the drop delay of the flow stream based on the first frequency and the second frequency. As discussed above, systems of interest may be fully automated, such as to reduce or entirely eliminate the need for user input or manual determination of drop delay of the flow cytometer. In embodiments, systems are configured to determine drop delay of the flow stream in the flow cytometer without the use of fluorescent particles (e.g., beads). For example, the systems may be configured to determine drop delay automatically during setup of the flow cytometer or in between analysis of different samples. In other words, determining the drop delay in certain embodiments may require little to no human intervention, manual input or initiation by the user.

As summarized above, systems include one or more imaging sensors configured to capture images of a flow cytometer flow stream in one or more detection fields. As described above, the term "detection field" refers to the region of the flow stream which is imaged by the one or more imaging sensors. Detection fields may vary depending on the properties of the flow stream being interrogated. In embodiments, the detection field may span 0.001 mm or more of the flow stream, such as 0.005 mm or more, such as 0.01 mm or more, such as 0.05 mm or more, such as 0.1 mm or more, such as 0.5 mm or more, such as 1 mm or more, such as 2 mm or more, such as 5 mm or more and including 10 mm or more of the flow stream. In embodiments, the detection field is a predetermined length of the flow stream. In some embodiments, the detection field includes the flow stream upstream from the flow stream break-off point and downstream from a sample interrogation point (e.g., laser interrogation point). By "break-off point" is meant the point in the flow stream where the continuous flow stream begins to form discrete droplets. In other embodiments, the detection field includes the flow stream downstream from a deflection plate, where the flow stream is subjected to an electrical charge upstream from the deflection plate. In some examples, the boundaries of the detection field include the flow cell nozzle orifice. In other examples, the boundaries of the detection field include the region where charged particles are deflected by deflector plates during cell sorting. In some embodiments, this location is distinct from the location of break off. In some embodiments, the detection field is offset from the location of droplet breakoff and the determined drop delay is adjusted with a fixed offset term.

Systems include one or more imaging sensors configured to capture images of a flow stream in a detection field. The imaging sensor may be any suitable device capable of capturing and converting an optical image into an electronic data signal, including but not limited to charge-coupled devices, semiconductor charge-coupled devices (CCD), active pixel sensors (APS), complementary metal-oxide semiconductor (CMOS) image sensors or N-type metal-oxide semiconductor (NMOS) image sensors. In some embodiments, the imaging sensor is a CCD camera. For example, the camera may be an electron multiplying CCD (EMCCD) camera or an intensified CCD (ICCD) camera. In other embodiments, the imaging sensor is a CMOS-type camera.

Depending on the length of the detection field being interrogated and size of the flow cytometer, the number of imaging sensors in the subject systems may vary, as desired. For example, the subject systems may include one imaging sensor or more, such as two imaging sensors or more, such as three imaging sensors or more, such as four imaging sensors or more, such as five imaging sensors or more and including ten imaging sensors or more. In certain embodiments, systems include one imaging sensor. In other embodiments, systems include two imaging sensors. Where systems include more than one imaging sensor, each imaging sensors may be oriented with respect to the other (as referenced in an X-Y plane) at an angle ranging from 10° to 90°, such as from 15° to 85°, such as from 20° to 80°, such as from 25° to 75° and including from 30° to 60°. In certain embodiments, each imaging sensor is oriented orthogonally (as referenced in an X-Y plane) to each other. For example, where the subject systems include two imaging sensors, the first imaging sensor is oriented orthogonally (as referenced in an X-Y plane) to the second imaging sensor.

Where the subject systems include more than one imaging sensor, each imaging sensor may be the same or a combination of sensors. For example, where the subject systems include two imaging sensors, in some embodiments the first imaging sensor is a CCD-type device and the second imaging sensor is a CMOS-type device. In other embodiments, both the first and second imaging sensor are CCD-type devices. In yet other embodiments, both the first and second imaging sensors are CMOS-type devices.

In some embodiments, the imaging sensors are stationary, maintaining a single position within the flow cytometer. In other embodiments, the imaging sensors may be configured to move along the path of the flow stream. For instance, the imaging sensor may be configured to move upstream and downstream alongside the flow stream capturing images in a plurality of detection fields. For example, systems may include an imaging sensor which is adapted to capture images in two or more different detection fields along the flow stream, such as a first detection field which includes the flow stream upstream from the flow stream break-off point and downstream from a sample interrogation point and a second detection field which includes the flow stream downstream from a deflection plate, where the flow stream is subjected to an electrical charge upstream from the deflection plate. Where the imaging sensor is configured to move along the flow stream, the imaging sensor may be moved along the flow stream path continuously or in discrete intervals. In some embodiments, the imaging sensor is displaced continuously. In other embodiments, the imaging sensor may be displaced along the flow stream path in discrete intervals, such as for example in 1 mm or greater increments, such as 2 mm or greater increments and including 5 mm or greater increments.

The imaging sensor may be configured to capture images continuously or in discrete intervals during application of each of the plurality of frequencies (as described above) by the oscillating transducer. In some instances, imaging sensors of interest are configured to capture images continuously. In other instances, imaging sensors are configured to take measurements in discrete intervals, such as capturing an image of the flow stream every 0.001 millisecond, every 0.01 millisecond, every 0.1 millisecond, every 1 millisecond, every 10 milliseconds, every 100 milliseconds and including every 1000 milliseconds, or some other interval.

As described in greater detail below, the imaging sensor is configured to capture one or more images of the flow stream in the detection field. For example, the imaging sensor may be configured to capture 2 or more images of the flow stream in the detection field, such as 3 or more images, such as 4 or more images, such as 5 or more images, such as 10 or more images, such as 15 or more images and including 25 or more images. Where a plurality of images are captured in the detection field, the processor may include digital imaging processing algorithm for combining, when desired, the plurality of images.

Depending on the flow stream rate and desired image resolution, the imaging sensor may have an exposure time of 100 ms or less when reading out the full sensor, such as 75 ms or less, such as 50 ms or less, such as 25 ms or less, such as 10 ms or less, such as 5 ms or less, such as 1 ms or less, such as 0.1 ms or less such as 0.01 ms or less, such as 0.001 ms or less, such as 0.0001 ms or less, such as 0.00001 ms or less and including an exposure time of 0.000001 ms or less. For example, the exposure time of the imaging sensor in the detection field which captures images of the flow stream in the detection field that includes the flow stream upstream from the flow stream break-off point and downstream from a sample interrogation point may have an exposure time which ranges from 0.0001 ms to 10 ms, such as from 0.001 ms to 5 ms, such as from 0.01 ms to 2 ms and including from 0.1 ms to 1 ms. Likewise, the exposure time of imaging sensors which captures images of the flow cytometer flow stream in a detection field that includes the flow stream downstream from a deflection plate may have an exposure time which ranges from 0.0001 ms to 10 ms, such as from 0.001 ms to 5 ms, such as from 0.01 ms to 2 ms and including from 0.1 ms to 1 ms.

In certain embodiments, imaging sensors in the subject systems may have 1M active pixels or more, such as 1.5M or more, e.g., 2M or more, 2.5M or more, or 3M or more. In certain aspects, a pixel corresponds to an actual physical dimension of about 0.3 μm. Depending on the detection field, in some instances, imaging sensors have a sensor area of 150 mm$^2$ or more, such as about 150 mm$^2$ to about 175 mm$^2$, about 175 mm$^2$ to about 200 mm$^2$, 200 mm$^2$ to about 225 mm$^2$, about 225 mm$^2$ to about 250 mm$^2$, about 250 mm$^2$ to about 300 mm$^2$, about 300 mm$^2$ to about 400 mm$^2$, about 400 mm$^2$ to about 500 mm$^2$, about 500 mm$^2$ to about 750 mm$^2$, about 750 mm$^2$ to about 1000 mm$^2$, or about 1000 mm$^2$ or more.

The imaging sensor may be positioned at any suitable distance from the flow cytometer flow stream so long as the sensor is capable of capturing an image of the flow stream in the detection field. For example, the imaging sensor may be positioned 0.01 mm or more from the flow stream, such as 0.05 mm or more, such as 0.1 mm or more, such as 0.5 mm or more, such as 1 mm or more, such as 2.5 mm or more, such as 5 mm or more, such as 10 mm or more, such as 15 mm or more, such as 25 mm or more and including 50 mm or more from the flow cytometer flow stream.

In some embodiments, the imaging sensor is positioned at an angle with respect to the flow stream axis. For example, the imaging sensor may be positioned at an angle with respect to the axis of the flow stream which ranges from 10° to 90°, such as from 15° to 85°, such as from 20° to 80°, such as from 25° to 75° and including from 30° to 60°. In certain embodiments, the imaging sensor is positioned at a 90° angle with respect to the axis of the flow stream.

In some instances, the imaging sensor also includes an optical adjustment protocol. By "optical adjustment" is meant that capturing images of the detection field by the imaging sensor may be changed as desired, such as to increase or decrease the captured dimensions or to enhance the optical resolution of the image. In some instances, optical adjustment is a magnification protocol configured to increase the size of the detection field captured by the imaging sensor, such as by 5% or greater, such as by 10% or greater, such as by 25% or greater, such as by 50% or greater and including increasing the detection field of the imaging sensor by 75% or greater. In other instances, optical adjustment is a de-magnification protocol configured to decrease the size of the detection field captured by the imaging sensor, such as by 5% or greater, such as by 10% or greater, such as by 25% or greater, such as by 50% or greater and including decreasing the size of the detection field captured by the imaging sensor by 75% or greater. In certain embodiments, optical adjustment is an enhanced resolution protocol configured to improve the resolution of the captured images, such as by 5% or greater, such as by 10% or greater, such as by 25% or greater, such as by 50% or greater and including enhancing the resolution of the captured images by 75% or greater. Capturing images of the detection field by the imaging sensor may be adjusted with any convenient optical adjustment protocol, including but not limited to lens, mirrors, filters and combinations thereof. In certain embodiments, the imaging sensor includes a focusing lens. The focusing lens, for example may be a de-magnifying lens. In other embodiments, the focusing lens is a magnifying lens.

Imaging sensors of the present disclosure may also include one or more wavelength separators. The term "wavelength separator" is used herein in its conventional sense to refer to an optical protocol for separating polychromatic light into its component wavelengths for detection. Wavelength separation, according to certain embodiments, may include selectively passing or blocking specific wavelengths or wavelength ranges of the polychromatic light. To separate wavelengths of light, the transmitted light may be passed through any convenient wavelength separating protocol, including but not limited to colored glass, bandpass filters, interference filters, dichroic mirrors, diffraction gratings, monochromators and combinations thereof, among other wavelength separating protocols. Systems may include one or more wavelength separators, such as two or more, such as three or more, such as four or more, such as five or more and including 10 or more wavelength separators. In one example, imaging sensors include one bandpass filter. In another example, imaging sensors include two or more bandpass filters. In another example, imaging sensors include two or more bandpass filters and a diffraction grating. In yet another example, imaging sensors include a plurality of bandpass filters and a monochromator. In certain embodiments, imaging sensors include a plurality of bandpass filters and diffraction gratings configured into a filter wheel setup. Where imaging sensors include two or more wavelength separators, the wavelength separators may be utilized individually or in series to separate polychromatic light into component wavelengths. In some embodiments, wavelength separators are arranged in series. In other embodiments, wavelength separators are arranged individually such that one or more measurements are conducted using each of the wavelength separators.

In some embodiments, systems include one or more optical filters, such as one or more bandpass filters. For example, in some instances the optical filters of interest are bandpass filters having minimum bandwidths ranging from 2 nm to 100 nm, such as from 3 nm to 95 nm, such as from 5 nm to 95 nm, such as from 10 nm to 90 nm, such as from 12 nm to 85 nm, such as from 15 nm to 80 nm and including bandpass filters having minimum bandwidths ranging from 20 nm to 50 nm. In other instances, the optical filters are longpass filters, such as for example longpass filters which attenuate wavelengths of light of 1600 nm or less, such as 1550 nm or less, such as 1500 nm or less, such as 1450 nm or less, such as 1400 nm or less, such as 1350 nm or less, such as 1300 nm or less, such as 1000 nm or less, such as 950 nm or less, such as 900 nm or less, such as 850 nm or less, such as 800 nm or less, such as 750 nm or less, such as 700 nm or less, such as 650 nm or less, such as 600 nm or less, such as 550 nm or less, such as 500 nm or less and including a longpass filter which attenuates wavelengths of light of 450 nm or less. In yet other instances, the optical filters are shortpass filters, such as for example shortpass filters which attenuate wavelengths of light of 200 nm or greater, such as 250 nm or greater, such as 300 nm or greater, such as 350 nm or greater, such as 400 nm or greater, such as 450 nm or greater, such as 500 nm or greater, such as 550 nm or greater and including shortpass filters which attenuate wavelengths of light of 600 nm or greater.

In other embodiments, the wavelength separator is a diffraction grating. Diffraction gratings may include, but are not limited to transmission, dispersive or reflective diffraction gratings. Suitable spacings of the diffraction grating may vary depending on the configuration of the light source, detection field and imaging sensor and other optical adjust protocols present (e.g., focusing lens), ranging from 0.01 μm to 10 μm, such as from 0.025 μm to 7.5 μm, such as from 0.5 μm to 5 μm, such as from 0.75 μm to 4 μm, such as from 1 μm to 3.5 μm and including from 1.5 μm to 3.5 μm.

In some embodiments, each imaging sensor is operably coupled to one or more light sources for illuminating the flow stream in the detection field. In some embodiments, the light source is a broadband light source, emitting light having a broad range of wavelengths, such as for example, spanning 50 nm or more, such as 100 nm or more, such as 150 nm or more, such as 200 nm or more, such as 250 nm or more, such as 300 nm or more, such as 350 nm or more, such as 400 nm or more and including spanning 500 nm or more. For example, one suitable broadband light source emits light having wavelengths from 200 nm to 1500 nm. Another example of a suitable broadband light source includes a light source that emits light having wavelengths from 400 nm to 1000 nm. Any convenient broadband light source protocol may be employed, such as a halogen lamp, deuterium arc lamp, xenon arc lamp, stabilized fiber-coupled broadband light source, a broadband LED with continuous spectrum, superluminescent emitting diode, semiconductor light emitting diode, wide spectrum LED white light source, an multi-LED integrated white light source, among other broadband light sources or any combination thereof. In certain embodiments, light sources for illuminating the flow stream in the detection field during image capture include an array of infra-red LEDs.

In other embodiments, the light source is a narrow band light source emitting a particular wavelength or a narrow range of wavelengths. In some instances, the narrow band light sources emit light having a narrow range of wavelengths, such as for example, 50 nm or less, such as 40 nm or less, such as 30 nm or less, such as 25 nm or less, such as 20 nm or less, such as 15 nm or less, such as 10 nm or less, such as 5 nm or less, such as 2 nm or less and including light sources which emit a specific wavelength of light (i.e., monochromatic light). Any convenient narrow band light source protocol may be employed, such as a narrow wavelength LED, laser diode or a broadband light source coupled to one or more optical bandpass filters, diffraction gratings, monochromators or any combination thereof.

As summarized above, systems include one or more processors operably coupled to the imaging sensors where the processors are configured to generate data signals from the captured images and to determine the drop delay of the flow stream. In embodiments, the processors include memory having a plurality of instructions for performing the steps of the subject methods (as described above), such as obtaining a first frequency (f1) of drop perturbation of a flow stream subjected to an oscillating vibration, capturing one or more images of the flow stream in a detection field, obtaining a second frequency (f2) of drop perturbation of the flow stream based on one or more of the captured images and determining the drop delay of the flow stream based on the first frequency and the second frequency. In certain embodiments, the subject systems are configured to generate data signals based on each of the first frequency, the second frequency and the calculated drop delay and adjust parameters of the flow cytometer in response to one or more of the data signals. For example, the amplitude and phase of drop perturbations applied by the oscillating transducer may be adjusted in response to data signals pertaining to the amplitude and phase of drop perturbations at the first frequency and the second frequency. In other instances, the flow rate of the flow stream, timing of applying an electrical charge or the drop charging voltage may be adjusted in response to the generated data signal corresponding to the calculated drop delay.

The subject systems may include both hardware and software components, where the hardware components may take the form of one or more platforms, e.g., in the form of servers, such that the functional elements, i.e., those elements of the system that carry out specific tasks (such as managing input and output of information, processing information, etc.) of the system may be carried out by the execution of software applications on and across the one or more computer platforms represented of the system. The processor includes memory having instructions stored thereon for performing the steps of the subject methods according to different embodiments described herein such as illuminating a flow cytometer flow stream in a detection field with a light source, capturing one or more images of the flow stream, obtaining a first frequency (f1) of drop perturbation of a flow stream subjected to an oscillating vibration, obtaining a second frequency (f2) of drop perturbation of the flow stream based on one or more of the captured images, determining the drop delay of the flow stream based on the first frequency and the second frequency and generating data signals corresponding to each of the first frequency, the second frequency and the calculated drop delay and adjust parameters of the flow cytometer in response to one or more of the generated data signals.

In embodiments, the processor is configured to obtain a first frequency (f1) and a second frequency (f2) of drop perturbations of a flow stream subjected to an oscillating vibration. The processor may be operably coupled to a transducer, such as a piezoelectric transducer for applying the oscillating vibration to the flow nozzle. In some embodiments, the memory includes instructions for applying a plurality of frequencies with the oscillating transducer and capturing one or more images at each of the different drop perturbation frequencies. For example, the memory may include instructions to sweep across a range of different drop perturbation frequencies, such as by varying the frequency of the oscillating transducer in a range from 1000 Hz to 50000 Hz, such as from 1500 Hz to 49500 Hz, such as from 2000 Hz to 49000 Hz, such as from 2500 Hz to 48500 Hz, such as from 5000 Hz to 45000 Hz, such as from 10000 Hz to 42500 Hz, such as from 15000 Hz to 40000 Hz and including varying the frequency of the oscillating transducer over a plurality of different frequencies in a range from 30000 Hz to 35000 Hz.

In certain embodiments, the processor includes memory having instructions for serially increasing the frequency of the oscillating transducer by 0.01 Hz or more, such as by 0.05 Hz or more, such as by 0.1 Hz or more, such as by 0.5 Hz or more, such as by 1 Hz or more, such as by 2 Hz or more, such as by 5 Hz or more, such as by 10 Hz or more, such as by 25 Hz or more, such as by 50 Hz or more, such as by 75 Hz or more and including by 100 Hz or more. For instance, in one example the memory includes instructions for applying serially increasing frequencies over a range at increments of 1 Hz or more (e.g., 10 Hz or more) from 1000 Hz to 10000 Hz, such as from 1500 Hz to 9000 Hz, such as from 2000 Hz to 8000 Hz, such as from 3000 Hz to 7000 Hz and including over a range at increments of 1 Hz or more (e.g., 10 Hz or more) from 4000 Hz to 6000 Hz. In another example, the memory includes instructions for applying serially increasing frequencies over a range at increments of 1 Hz or more (e.g., 10 Hz or more) from 10000 Hz to 20000 Hz, such as from 11000 Hz to 19000 Hz, such as from 12000 Hz to 18000 Hz, such as from 13000 Hz to 17000 Hz, and including at increments of 1 Hz or more (e.g., 10 Hz or more) from 14000 Hz to 16000 Hz. In yet another example, the memory includes instructions for applying serially increasing frequencies over a range at increments of 1 Hz or more (e.g., 10 Hz or more) from 20000 Hz to 30000 Hz, such as from 21000 Hz to 29000 Hz, such as from 22000 Hz to 28000 Hz, such as from 23000 Hz to 27000 Hz, and including at increments of 1 Hz or more (e.g., 10 Hz or more) from 24000 Hz to 26000 Hz. In still other examples, the memory includes instructions for applying serially increasing frequencies over a range at increments of 1 Hz or more (e.g., 10 Hz or more) from 30000 Hz to 35000 Hz, such as from 30500 Hz to 34000 Hz, such as from 31000 Hz to 33500 Hz and including at increments of 1 Hz or more (e.g., 10 Hz or more) from 30000 Hz to 32000 Hz.

In certain embodiments, the processor includes memory having instructions stored thereon for setting the drive frequency of an oscillating transducer to 5 incrementally increasing frequencies: $a_1$, $a_2$, $a_3$, $a_4$, and $a_5$ and capturing one or more images at each of frequencies $a_1$, $a_2$, $a_3$, $a_4$, and $a_5$. The instructions further include algorithm which designates $a_1$ to be the first frequency (f1) and algorithm which determines the second frequency from one of $a_2$, $a_3$, $a_4$, and $a_5$ based on the captured images at these frequencies. For example, the memory may include instructions for setting the drive frequency of an oscillating transducer to 5 different frequencies in the range from 30000 Hz to 32000 Hz (e.g., $a_1$=30000 Hz; $a_2$=30500 Hz; $a_3$=31000 Hz, $a_4$=31500 Hz and $a_5$=32000 Hz) and capturing one or more images at each of these frequencies. The instructions include algorithm which designates the first frequency to be 30000 Hz and algorithm for obtaining the second frequency from 30500 Hz, 31000 Hz, 31500 Hz and 32000 Hz based on the captured images at these frequencies.

In some embodiments, the detection field is downstream from a deflection plate and the memory of the processor further includes instructions for applying an electrical charge to the flow stream upstream from the deflection plate and algorithm for determining the first frequency and second frequency from one or more captured images of a deflected flow stream. In these embodiments, the memory includes instructions having algorithm for designating the first frequency as the frequency of the oscillating transducer when one or more of the captured images begins to show a deflection of flow stream drops in the detection field and algorithm for designating the second frequency as the frequency of the oscillating transducer when the captured images exhibits maximal stream deflection by the deflection plate.

In certain embodiments, the memory includes instructions for adjusting the drop charge voltage in order to determine the second frequency. For example, the memory may include instructions for increasing the drop charging voltage such as by 0.01 V or more, such as 0.05 V or more, such as 0.1 V or more, such as by 0.5V or more, such as by 1V or more, such as by 5V or more, such as by 10V or more, such as by 15V or more, such as by 25V or more, such as by 50V or more and including increasing the drop charging voltage by 75V or more. In other instances, the memory may include instructions for reducing the drop charging voltage, such as by 0.01 V or more, such as 0.05 V or more, such as 0.1 V or more, such as by 0.5V or more, such as by 1V or more, such as by 5V or more, such as by 10V or more, such as by 15V or more, such as by 25V or more, such as by 50V or more and including reducing the drop charging voltage by 75V or more.

In embodiments, the memory includes algorithm for determining the first and second frequency using the captured images at each of different frequencies of the oscillating transducer and does not include algorithm for determining these frequencies based on a detection of current from the charged flow stream drops.

In embodiments of the present disclosure, systems of interest are configured for determining drop delay based on the obtained first frequency (f1) and the second frequency (f2). In certain embodiments, memory operably coupled to the processor includes algorithm for generating data signals corresponding to the first frequency (f1) and the second frequency (f2) and calculating drop delay based on the data signals. In certain embodiments, drop delay is calculated according to Formula 1:

Drop Delay=[$f1/(f2-f1)$]   Formula 1 where drop delay is expressed as the number of drop periods in the detection field (e.g., a detection field that includes the flow stream upstream from the flow stream break-off point and downstream from the laser interrogation point or a detection field that includes a deflected flow stream downstream from a deflection plate).

In certain other embodiments, drop delay is calculated according to Formula 2:

Drop Delay=[$f1/(f2-f1)$]+$o1$+$o2$   Formula 2 where terms have the meanings described in Formula 1, together with two introduced offset terms $o1$ and $o2$. $o1$ refers to the offset in drop delay introduced by use of a image feature that is not the drop breakoff point when measuring similarity. $o2$ refers to the offset in drop delay introduced by acquiring the first and second images at a time that is not the moment of breakoff.

As described above, each of the plurality of frequencies used in determining the first frequency and second frequency is maintained at a constant amplitude and phase. In some embodiments, systems of interest include memory having instructions for determining and if necessary, adjusting one or more of the amplitude and phase of drop perturbations at each of the plurality of different frequencies. As discussed above, the amplitude and phase at each of the different drop perturbation frequencies may be determined by irradiating the flow stream subjected to an oscillating vibration with light and detecting the refraction of light by the drop perturbations.

In some embodiments, systems of interest include memory having instructions for determining image similarity between two features in the first and second images and adjusting the amplitude of drop perturbations at each of the plurality of different frequencies to obtain maximal similarity, regardless of the spatial position of these features.

The light source for determining amplitude and phase of drop perturbations may be any suitable broadband or narrow band source of light. The light source may be configured to emit wavelengths of light that vary, ranging from 200 nm to 1500 nm, such as from 250 nm to 1250 nm, such as from 300 nm to 1000 nm, such as from 350 nm to 900 nm and including from 400 nm to 800 nm. For example, the light source may include a broadband light source emitting light having wavelengths from 200 nm to 900 nm. In other instances, the light source includes a narrow band light source emitting a wavelength ranging from 200 nm to 900 nm. For example, the light source may be a narrow band LED (1 nm-25 nm) emitting light having a wavelength ranging between 200 nm to 900 nm. In some embodiments, the light source is a laser, such as continuous wave laser. For example, the laser may be a diode laser, such as a ultraviolet diode laser, a visible diode laser and a near-infrared diode laser. In some instances, the diode laser outputs light at wavelengths ranging from 375 nm to 1000 nm, such as from 405 nm to 875 nm, such as from 450 nm to 800 nm, such as from 500 nm to 650 nm and including from 525 nm to 625 nm. In certain embodiments, lasers of interest include a 405 nm diode laser. In other embodiments, the laser may be a helium-neon (HeNe) laser. In certain embodiments, the light source is a laser in a flow cytometer. In some instances, the subject systems include a gas laser, such as a helium-neon laser, argon laser, krypton laser, xenon laser, nitrogen laser, $CO_2$ laser, CO laser, argon-fluorine (ArF) excimer laser, krypton-fluorine (KrF) excimer laser, xenon chlorine (XeCl) excimer laser or xenon-fluorine (XeF) excimer laser or a combination thereof. In others instances, the subject systems include a dye laser, such as a stilbene, coumarin or rhodamine laser. In yet other instances, lasers of interest include a metal-vapor laser, such as a helium-cadmium (HeCd) laser, helium-mercury (HeHg) laser, helium-selenium (HeSe) laser, helium-silver (HeAg) laser, strontium laser, neon-copper (NeCu) laser, copper laser or gold laser and combinations thereof. In still other instances, the subject systems include a solid-state laser, such as a ruby laser, an Nd:YAG laser, NdCrYAG laser, Er:YAG laser, Nd:YLF laser, Nd:YVO$_4$ laser, Nd:YCa$_4$O(BO$_3$)$_3$ laser, Nd:YCOB laser, titanium sapphire laser, thulium YAG laser, ytterbium YAG laser, ytterbium$_2$O$_3$ laser or cerium doped lasers and combinations thereof. In certain embodiments, the light source is a low power laser (e.g., a 650 nm laser outputting 5 mW).

In other embodiments, the light source is a non-laser light source, such as a lamp, including but not limited to a halogen lamp, deuterium arc lamp, xenon arc lamp, a light-emitting diode, such as a broadband LED with continuous spectrum, superluminescent emitting diode, semiconductor light emitting diode, wide spectrum LED white light source, an multi-LED integrated. In some instances the non-laser light source is a stabilized fiber-coupled broadband light source, white light source, among other light sources or any combination thereof.

The light source used to monitor amplitude and phase of drop perturbations in the flow stream may be positioned at any suitable distance from the flow stream, such as at a distance of 0.001 mm or more from the flow stream, such as 0.005 mm or more, such as 0.01 mm or more, such as 0.05 mm or more, such as 0.1 mm or more, such as 0.5 mm or more, such as 1 mm or more, such as 5 mm or more, such as 10 mm or more, such as 25 mm or more and including at a distance of 100 mm or more from the flow stream. In addition, the light source may be positioned at any suitable angle to the vertical axis of the flow stream (i.e., the angle the beam of irradiation makes with the vertical axis of the flow stream), such as at an angle ranging from 10° to 90°, such as from 15° to 85°, such as from 20° to 80°, such as from 25° to 75° and including from 30° to 60°. In certain embodiments, the light source is positioned at a 90° angle with respect to the vertical axis of the flow stream (i.e., the light source is orthogonal to the vertical axis of the flow stream)

The light source may be configured to irradiate the flow stream continuously or in discrete intervals. In some instances, systems include a light source that is configured to irradiate the flow stream continuously, such as with a continuous wave laser that continuously irradiates the flow stream at the interrogation point in a flow cytometer. In other instances, systems of interest include a light source that is configured to irradiate the flow stream at discrete intervals, such as every 0.001 milliseconds, every 0.01 milliseconds, every 0.1 milliseconds, every 1 millisecond, every 10 milliseconds, every 100 milliseconds and including every 1000 milliseconds, or some other interval. Where the light source is configured to irradiate the flow stream at discrete intervals, systems may include one or more additional components to provide for intermittent irradiation of the flow stream with the light source. For example, the subject systems in these embodiments may include one or more laser beam choppers, manually or computer controlled beam stops for blocking and exposing the flow stream to the light source.

As discussed above, in assessing alignment of the light source with the flow stream, first and second light signals are detected along a vertical axis of the irradiated flow stream. In embodiments, the subject systems include one or more photodetectors for detecting light signals from the flow stream. Photodetectors in the subject systems may be any convenient positional sensing detecting protocol, including but not limited to photosensors or photodetectors, such as active-pixel sensors (APSs), quadrant photodiodes, image sensors, charge-coupled devices (CCDs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, the systems of interest include a quadrant photodiode, e.g., as described in U.S. Provisional Application Ser. No. 62/091,421; the disclosure of which is herein incorporated by reference. For example the photodetector may be a quadrant photodiode having an active detecting surface area of each region that ranges from 0.01 $cm^2$ to 10 $cm^2$, such as from 0.05 $cm^2$ to 9 $cm^2$, such as from, such as from 0.1 $cm^2$ to 8 $cm^2$, such as from 0.5 $cm^2$ to 7 $cm^2$ and including from 1 $cm^2$ to 5 $cm^2$. In some instances, the photodetector is a photodiode array having more than one photodiode, such as two or more photodiodes, such as three or more, such as five or more and including 10 or more photodiodes.

The photodetector may be positioned at any suitable distance from the flow stream so long as a usable light signal is detectable. For example, detectors in the subject systems may be positioned 1 mm or more from the flow stream, such as 5 mm or more, such as 10 mm or more, such as 15 mm or more, such as 25 mm or more, such as 50 mm or more, such as 100 mm or more, such as 150 mm or more, such as 250 mm or more and including 500 mm or more from the flow stream. The detectors may also be positioned at any angle from the flow stream. For example, the detectors may be angled with respect to the vertical axis of the flow stream at from 10° to 90°, such as from 15° to 85°, such as from 20° to 80°, such as from 25° to 75° and including from 30° to 60°. In some instances, the one or more detectors are positioned at 30° to 60° with respect to the vertical axis of the flow stream.

In certain embodiments, the subject systems are configured to assess the amplitude and phase of drop perturbations in the flow stream by forward propagated (e.g., scattered) light from the irradiated flow stream and include one or more detectors positioned adjacent to the flow stream in a forward configuration from the light source. For example, the light signals from the irradiated flow stream may be detected by one or more detectors configured as forward scatter detectors. In these embodiments, the forward scatter detectors are positioned on the opposite side of the flow stream from the light source and are positioned to collect and detect forward propagated (e.g., scattered) light. In other embodiments, the subject systems are configured to assess the amplitude and phase of drop perturbations in the flow stream by detecting light signals from light propagated upstream by total internal reflectance. In certain embodiments, flow cell nozzles and systems of interest for detecting light signals from light propagated upstream by total internal reflectance in a flow cytometer include, but are not limited to those described in U.S. patent application Ser. No. 14/260,177 filed on Apr. 23, 2014 and published as US2014/0320861, the disclosure of which is herein incorporated by reference.

Systems may include any convenient positional sensing detecting protocol to detect the light signals refracted by the drop perturbations in the flow stream, such as, but not limited to photosensors or photodetectors, such as active-pixel sensors (APSs), quadrant photodiodes, wedge detectors image sensors, charge-coupled devices (CCDs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In one embodiment, the light signals are detected with a quadrant photodiode. In other embodiments, systems include a "wedge" detector, such as described in U.S. Pat. No. 7,362,424, the disclosure of which is herein incorporated by reference. The active detecting surface area of each region of the position sensing detector (e.g., quadrant photodiode) may vary, such as from 0.01 $cm^2$ to 10 $cm^2$, such as from 0.05 $cm^2$ to 9 $cm^2$, such as from 0.1 $cm^2$ to 8 $cm^2$, such as from 0.5 $cm^2$ to 7 $cm^2$ and including from 1 $cm^2$ to 5 $cm^2$.

In embodiments, the processor is configured to calculate the difference in amplitude between the first light signal and the second light signal to determine a differential signal. In some embodiments, the processor includes algorithm to calculate the differential signal between the first and second light signals in conjunction with detecting the first and second light signals. In other embodiments, the processor includes algorithm to calculate the differential signal at a predetermined duration following detection of the light signals, such as 0.001 microseconds or longer after detection of the first and second light signals, such as 0.01 microseconds or longer, such as 0.1 microseconds or longer, such as 0.5 microseconds or longer, such as 1 microsecond or longer, such as 2 microseconds or longer, such as 5 microseconds or longer, such as 10 microseconds or longer, such as 100 microseconds or longer, such as 500 microseconds or longer and including 1000 microseconds or longer after detection of the first and second light signals.

In certain embodiments, systems of interest are configured to adjust the amplitude and phase of the drop perturbations at each of the plurality of frequencies in response to the assessed amplitude and phase. In some embodiments, the memory includes algorithm for increasing the amplitude of the oscillating transducer, such as by increasing the amplitude by 1% or more, such as by 5% or more, such as by 10% or more, such as by 25% or more, such as by 50% or more and including by 2-fold or more, such as 3-fold or more, such as 4-fold or more and including by increasing the amplitude of the oscillating transducer by 5-fold or more. In other embodiments, the memory includes algorithm for decreasing the amplitude of the oscillating transducer, such as by decreasing the amplitude by 1% or more, such as by 5% or more, such as by 10% or more, such as by 25% or more, such as by 50% or more and including by 2-fold or more, such as 3-fold or more, such as 4-fold or more and including by decreasing the amplitude of the oscillating transducer by 5-fold or more. In other embodiments, the memory includes algorithm for introducing a full or partial phase shift to the phase of the drop perturbations determined from the differential signal. For example, the memory may include algorithm for introducing a phase shift of $\pi/64$ or more, such as a phase shift of $\pi/32$, such as a phase shift of $\pi/16$, such as a phase shift of $\pi/8$, such as a phase shift of $\pi/4$, such as a phase shift of $\pi/2$ and including a full phase shift of $\pi$ to the phase of the drop perturbations determined from the differential signal.

In certain embodiments, the subject systems include flow cytometer systems employing flow cell nozzles and optics subsystems for detecting light emitted by a sample in a flow stream. Suitable flow cytometer systems and methods for analyzing samples include, but are not limited to those described in Ormerod (ed.), *Flow Cytometry: A Practical Approach*, Oxford Univ. Press (1997); Jaroszeski et al. (eds.), *Flow Cytometry Protocols*, Methods in Molecular Biology No. 91, Humana Press (1997); *Practical Flow Cytometry*, 3rd ed., Wiley-Liss (1995); Virgo, et al. (2012) *Ann Clin Biochem*. January; 49 (pt 1):17-28; Linden, et. al., *Semin Throm Hemost*. 2004 October; 30(5):502-11; Alison, et al. *J Pathol*, 2010 December; 222(4):335-344; and Herbig, et al. (2007) *Crit Rev Ther Drug Carrier Syst*. 24(3): 203-255; the disclosures of which are incorporated herein by reference. In certain instances, flow cytometry systems of interest include BD Biosciences FACSCanto™ flow cytometer, BD Biosciences FACSVantage™, BD Biosciences FACSort™, BD Biosciences FACSCount™, BD Biosciences FACScan™, and BD Biosciences FACSCalibur™ systems, a BD Biosciences Influx™ cell sorter, BD Biosciences Jazz™ cell sorter and BD Biosciences Aria™ cell sorter or the like.

In certain embodiments, the subject systems are flow cytometer systems which incorporate one or more components of the flow cytometers described in U.S. Pat. Nos. 3,960,449; 4,347,935; 4,667,830; 4,704,891; 4,770,992; 5,030,002; 5,040,890; 5,047,321; 5,245,318; 5,317,162; 5,464,581; 5,483,469; 5,602,039; 5,620,842; 5,627,040; 5,643,796; 5,700,692; 6,372,506; 6,809,804; 6,813,017; 6,821,740; 7,129,505; 7,201,875; 7,544,326; 8,140,300; 8,233,146; 8,753,573; 8,975,595; 9,092,034; 9,095,494 and 9,097,640; the disclosures of which are herein incorporated by reference.

In certain embodiments, flow cytometers of interest are configured to include a flow cell nozzle which is configured to propagate light emitted by a sample in a flow stream upstream through the nozzle orifice by total internal reflectance. The term "propagate" is used herein in its conventional sense to refer to the travel of light through the fluid medium of the flow stream where the path of propagated light is a function of the refraction, reflection, diffraction and interference by the fluid medium. In these embodiments, the flow cytometer includes a flow cell nozzle that propagates and collects light in a direction which is opposite to the direction of fluid flow by the flow stream. In other words, where the flow stream has fluidic flow along the positive Y direction along the Y axis in an X-Y plane, light signals from light propagated upstream by total internal reflectance traverses in the negative Y direction. The phrase "total internal reflectance" is used herein in its conventional sense to refer to the propagation of electromagnetic waves within the boundaries of a fluid medium (e.g., flow stream) such that when a propagating wave strikes the medium boundary at an angle larger than the critical angle with respect to the normal to the surface, the electromagnetic wave is internally reflected.

Flow cell nozzles according to these embodiments includes a nozzle chamber having a proximal end where light propagated upstream is collected and a distal end having a nozzle orifice in fluid communication with the flow stream. In some instances, the flow cell nozzle includes a proximal cylindrical portion defining a longitudinal axis and a distal frustoconical portion which terminates in a flat surface having the nozzle orifice that is transverse to the longitudinal axis. The angle of the frustoconical walls of the flow nozzle relative to the longitudinal axis of the flow stream may vary, in certain embodiments, ranging from 120° to 160°. In certain embodiments, the walls of the nozzle chamber are reflective. The proximal end of the flow cell nozzle in flow cytometers of interest may include a sample injection port to provide sample (e.g., a biological sample) to the flow cell and a sheath fluid injection port which provides sheath fluid to the flow cell nozzle.

In some instances, the flow cell nozzle includes one or more optical adjustment components. By "optical adjustment" is meant that emitted light propagated upstream from the flow stream through the nozzle orifice is changed as desired before being conveyed to a detector (as discussed in greater detail below) for measurement. For example, the optical adjustment may be to increase the dimensions of the collected beam of light, to focus the collected beam of light onto the surface of a detector or to collimate the beam of light. In some instances, optical adjustment is a magnification protocol so as to increase the beam spot produced by the light beam propagated through the nozzle orifice by total internal reflectance within the flow stream. In other instances, optical adjustment is a focusing protocol to reduce the dimensions of the beam spot.

In some embodiments, flow cell nozzles and flow cytometer systems of interest that are configured to propagate light emitted by a sample upstream through the flow stream by total internal reflectance include those described in U.S.

patent application Ser. No. 14/260,177 filed on Apr. 23, 2014, the disclosure of which is herein incorporated by reference.

In some embodiments, the subject systems include flow cytometer systems that also employ the imaging sensors and optics subsystems described herein to assess alignment of the light source with the flow stream. The phrase "assessing alignment" is used herein in its conventional sense to refer to determining the relative position of irradiation on the flow stream by the light source. In some embodiments, assessing alignment of the light source with the flow stream includes determining the position of irradiation by the light source along the horizontal axis of the flow stream. As discussed above, systems of interest may include one or more light sources (e.g., laser, such as a diode laser) and one or more position sensing detectors (e.g., quadrant photodiode or wedge detector) Systems of interest according to these embodiments may also include in the memory operably coupled to the processor, instructions to calculate a differential signal amplitude between a first light signal and a second light signal to assess alignment of a light source (e.g., laser) with a flow stream. In embodiments, the processor is configured to execute instructions from memory for assessing alignment of the light source with the flow stream and in some instances, adjust the position of the light source to match a position which produces the maximal differential signal amplitude between the first light signal and the second light signal from the irradiated flow stream. The memory operably coupled to processors described herein may include a plurality of instructions for detecting first and second light signals at different times along a vertical axis of the irradiated flow stream, calculating a differential signal amplitude between the first signal and second signal and assessing alignment of the light source with the flow stream based on the calculated differential signal amplitude between the first light signal and second light signal.

In some instances, the processor memory described herein further includes algorithm for determining a maximal differential signal amplitude to assess alignment of the flow stream with the light source. For example, the processor memory may include algorithm for determining the position of irradiation by the light source on the flow stream that produces the maximal differential signal amplitude between the first light signal and the second lights signal. In this example, systems of interest may use one or more image capturing sensors described herein for mapping the spatial position of the irradiation on the flow stream in an X-Y plane. In some instances, the subject systems are configured to adjust the position of the light source in response to the assessed alignment between the light source and the flow stream. The subject systems may also be configured to automatically align the light source with flow stream.

In some embodiments, systems of interest that are configured to assess the alignment of a light source with the flow stream include those described in U.S. Provisional Patent Application No. 62/091,421 filed on Dec. 12, 2014, the disclosure of which is herein incorporated by reference.

In some embodiments, the flow cytometers are flow cytometers that include one or more components from the cytometers described in: U.S. application Ser. No. 14/260, 177 published as US2014/0320861; U.S. Provisional Application Ser. No. 62/090,248 and U.S. Provisional Application Ser. No. 62/091,421; the disclosures of which are herein incorporated by reference.

Computer-Readable Storage Medium for Determining Drop Delay of Flow Cytometer Flow Stream Aspects of the present disclosure further include non-transitory computer readable storage mediums having instructions for practicing the subject methods. Computer readable storage mediums may be employed on one or more computers for complete automation or partial automation of a system for practicing methods described herein. In certain embodiments, instructions in accordance with the method described herein can be coded onto a computer-readable medium in the form of "programming", where the term "computer readable medium" as used herein refers to any non-transitory storage medium that participates in providing instructions and data to a computer for execution and processing. Examples of suitable non-transitory storage media include a floppy disk, hard disk, optical disk, magneto-optical disk, CD-ROM, CD-R, magnetic tape, non-volatile memory card, ROM, DVD-ROM, Blue-ray disk, solid state disk, and network attached storage (NAS), whether or not such devices are internal or external to the computer. A file containing information can be "stored" on computer readable medium, where "storing" means recording information such that it is accessible and retrievable at a later date by a computer. The computer-implemented method described herein can be executed using programming that can be written in one or more of any number of computer programming languages. Such languages include, for example, Java (Sun Microsystems, Inc., Santa Clara, Calif.), Visual Basic (Microsoft Corp., Redmond, Wash.), and C++ (AT&T Corp., Bedminster, N.J.), as well as any many others.

In some embodiments, computer readable storage media of interest include a computer program stored thereon, where the computer program when loaded on the computer includes instructions having: algorithm for obtaining a first frequency of drop perturbation of a flow stream subjected to an oscillating vibration; algorithm for capturing one or more images in a detection field of the flow stream with an imaging sensor; algorithm for obtaining a second frequency of drop perturbation of the flow stream based on one or more of the captured images; and algorithm for determining the drop delay of the flow stream based on the first frequency and the second frequency.

The computer readable storage medium may include instructions for capturing one or more images of the flow stream in the detection field, such as 2 or more images of the flow stream in the detection field, such as 3 or more images, such as 4 or more images, such as 5 or more images, such as 10 or more images, such as 15 or more images and including 25 or more images. In certain embodiments, the computer readable storage medium includes instructions for optical adjustment of the captured images, such as to enhance the optical resolution of the image. In certain embodiments, computer readable storage medium may include instructions for enhancing the resolution of the captured images by 5% or greater, such as by 10% or greater, such as by 25% or greater, such as by 50% or greater and including enhancing the resolution of the captured images by 75% or greater.

In embodiments, computer readable storage media of interest include instructions for obtaining a first frequency (f1) and a second frequency (f2) of drop perturbations of a flow stream subjected to an oscillating vibration. In some embodiments, instructions include applying a plurality of frequencies with the oscillating transducer and capturing one or more images at each of the different drop perturbation frequencies. For example, the memory may include instructions to sweep across a range of different drop perturbation frequencies, such as by varying the frequency of the oscillating transducer in a range from 1000 Hz to 50000 Hz, such as from 1500 Hz to 49500 Hz, such as from 2000 Hz to 49000 Hz, such as from 2500 Hz to 48500 Hz, such as from 5000 Hz to 45000 Hz, such as from 10000 Hz to 42500 Hz, such as from 15000 Hz to 40000 Hz and including varying the frequency of the oscillating transducer over a plurality of different frequencies in a range from 30000 Hz to 35000 Hz.

As described above, in certain embodiments the detection field is downstream from a deflection plate and the computer readable storage medium includes instructions for applying an electrical charge to the flow stream upstream from the deflection plate and algorithm for determining the first frequency and second frequency from one or more captured images of a deflected flow stream. In these embodiments, the computer readable storage medium includes instructions having algorithm for designating the first frequency as the frequency of the oscillating transducer when one or more of the captured images begins to show a deflection of flow stream drops in the detection field and algorithm for designating the second frequency as the frequency of the oscillating transducer when the captured images exhibits maximal stream deflection by the deflection plate.

Computer readable storage medium according to embodiments of the present disclosure also include algorithm for calculating drop delay based on the obtained first frequency (f1) and the second frequency (f2). In certain embodiments, the computer readable storage medium algorithm for generating data signals corresponding to the first frequency (f1) and the second frequency (f2) and calculating drop delay based on the data signals. In certain embodiments, drop delay is calculated according to Formula 1:

$$\text{Drop Delay} = [f1/(f2-f1)] \quad \text{Formula 1}$$

where drop delay is expressed as the number of drop periods in the detection field (e.g., a detection field that includes the flow stream upstream from the flow stream break-off point and downstream from the laser interrogation point or a detection field that includes a deflected flow stream downstream from a deflection plate).

In certain other embodiments, drop delay is calculated according to Formula 2:

$$\text{Drop Delay} = [f1/(f2-f1)] + o1 + o2 \quad \text{Formula 2}$$

where terms have the meanings described in formula 1, together with two introduced offset terms o1 and o2. o1 refers to the offset in drop delay introduced by use of a similarity feature that is not the drop breakoff point. o2 refers to the offset in drop delay introduced by acquiring the first and second images at a time that is not the moment of breakoff.

In certain embodiments, the computer readable storage medium includes algorithm for assessing the amplitude and phase of drop perturbations in the flow stream. In these embodiments, the computer readable storage medium includes instructions for irradiating the flow stream with a light source (e.g., a laser) and algorithm for positioning a detector to collect forward propagated (e.g., scattered) light from the irradiated flow stream. The computer readable storage medium includes algorithm for calculating a differential signal from a first light signal and a second light signal and determining the amplitude and phase of drop perturbations at each of the plurality frequencies based on the differential signal.

The computer readable storage medium may be employed on one or more computer systems having a display and operator input device. Operator input devices may, for example, be a keyboard, mouse, or the like. The processing module includes a processor which has access to a memory having instructions stored thereon for performing the steps of the subject methods. The processing module may include an operating system, a graphical user interface (GUI) controller, a system memory, memory storage devices, and input-output controllers, cache memory, a data backup unit, and many other devices. The processor may be a commercially available processor or it may be one of other processors that are or will become available. The processor executes the operating system and the operating system interfaces with firmware and hardware in a well-known manner, and facilitates the processor in coordinating and executing the functions of various computer programs that may be written in a variety of programming languages, such as Java, Perl, C++, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques.

Figure 5:
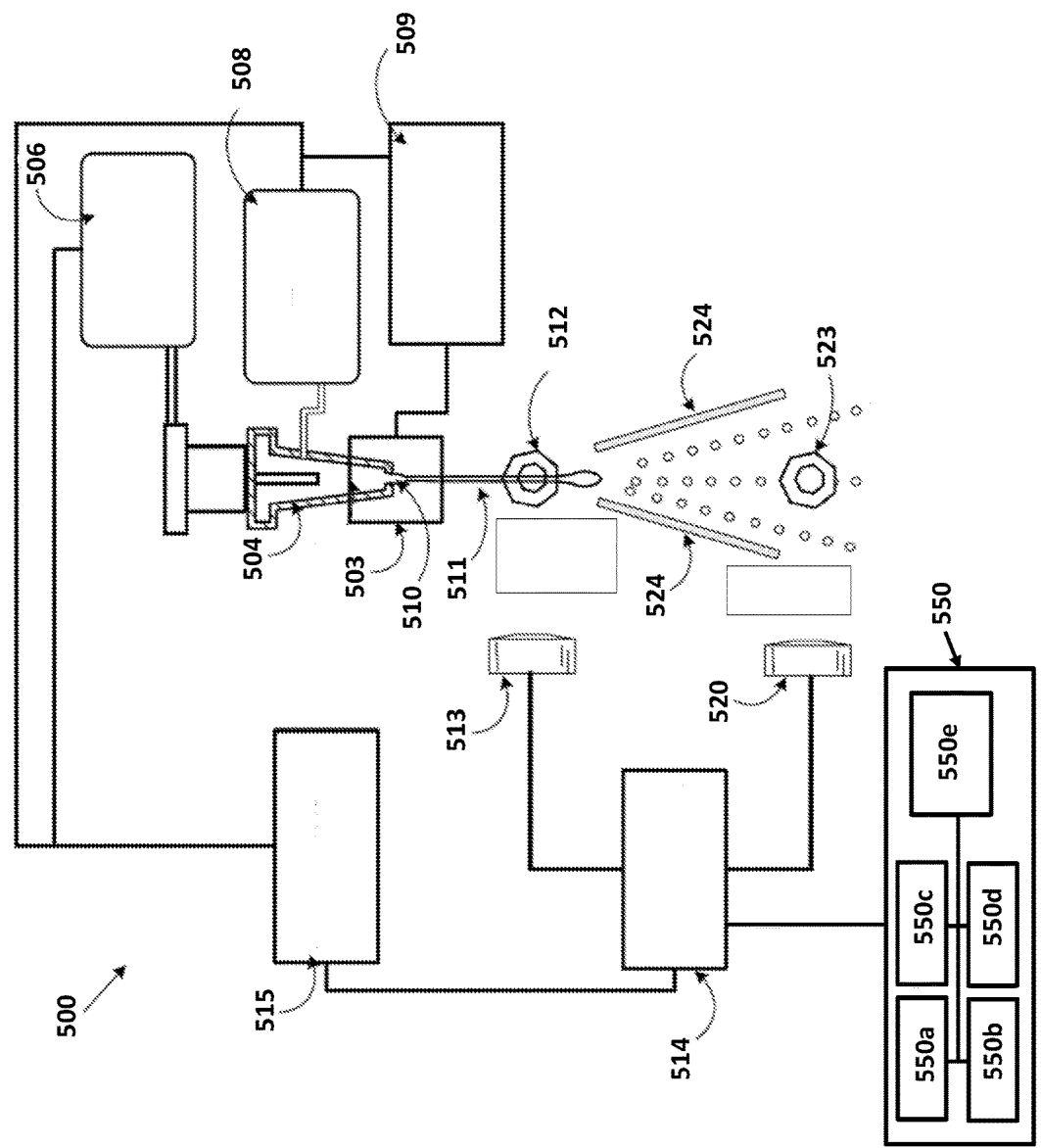
FIG. 5 depicts a system for determining drop delay of a flow cytometer according to certain embodiments.

A flow cytometer 500 employing an embodiment of the present invention is illustrated in FIG. 5. Flow cytometer 100 includes flow cell 504, a sample reservoir 506 for providing a fluid sample, (e.g., blood sample), to the flow cell and a sheath reservoir 508 for providing a sheath fluid to the flow cell with fluidics subsystem 515. Flow cytometer 500 is configured to transport fluid sample having cells in a flow stream to flow cell 504 in conjunction with a laminating flow of sheath fluid. Analysis of the flow stream at an interrogation zone 503 with imaging sensor system 509 as described herein. The flow stream exits the flow cell 504 through a nozzle orifice 510 as flow stream 511. Flow stream 511 may be sorted as droplets using droplet deflector plates 524.

Imaging cameras 513 and 520 or other image collection devices (as described above) may be positioned to capture an image of the flow stream in a first detection field (512) or a second detection field (523). Imaging sensor 509 and imaging cameras 513 and 520 are controlled by processor 514. Processor 514 may be operationally coupled to a non-transitory computer readable storage medium 550 having instructions stored thereon for determining drop delay of a flow stream in flow cytometer 500. In certain embodiments, non-transitory computer readable storage medium 550 includes algorithm for obtaining a first frequency of drop perturbation of a flow stream subjected to an oscillating vibration (550a); algorithm for capturing one or more images in a detection field of the flow stream with an imaging sensor (550b); algorithm for obtaining a second frequency of drop perturbation of the flow stream based on one or more of the captured images (550c); algorithm for determining one or more of the amplitude and phase of drop perturbations at the first frequency and the second frequency (550d); and algorithm for determining the drop delay of the flow stream based on the first frequency and the second frequency (550e).

Utility

The subject methods, systems, and computer readable storage medium find use in a variety of different applications where it is desirable to accurately and conveniently determine drop delay of a flow cytometer. The present disclosure also finds use in automating calibration and setup of a flow cytometer so as to provide for fast, reliable systems for characterizing and sorting cells from a biological sample. Embodiments of the present disclosure find use where minimizing the amount of reliance on human input and adjustments to the system are desired, such as in research and high throughput laboratory testing. The present disclosure also finds use where it is desirable to provide a flow cytometer with improved cell sorting accuracy, enhanced particle collection, particle charging efficiency, more accurate particle charging and enhanced particle deflection during cell sorting. In embodiments, the present disclosure reduces the need for user input or manual adjustment to set up the flow cytometer or between sample analysis with the flow cytometer. In certain embodiments, the subject systems provide fully automated protocols so that calculation of the drop delay of the flow cytometer as well as adjustments to parameters of the flow cytometer that rely on an accurate drop delay (e.g., timing of flow stream charging) require little, if any human input.

The present disclosure also finds use in applications where cells prepared from a biological sample may be desired for research, laboratory testing or for use in therapy. In some embodiments, the subject methods and devices may facilitate the obtaining individual cells (i.e., single cell resolution) prepared from a target fluidic or tissue biological sample. For example, the subject methods and systems facilitate obtaining cells from fluidic or tissue samples to be used as a research or diagnostic specimen for diseases such as cancer. Likewise, the subject methods and systems facilitate obtaining cells from fluidic or tissue samples to be used in therapy. Methods, systems and computer readable storage media described herein allow for separating and collecting cells from a biological sample (e.g., organ, tissue, tissue fragment, fluid) with enhanced efficiency and low cost as compared to traditional flow cytometry systems.

Notwithstanding the appended clauses, the disclosure set forth herein is also defined by the following clauses:

1. A method of determining drop delay of a flow stream in a flow cytometer, the method comprising:
obtaining a first frequency (f1) of drop perturbation of a flow stream subjected to an oscillating vibration;
capturing one or more images of the flow stream in a detection field;
obtaining a second frequency (f2) of drop perturbation of the flow stream based on one or more of the captured images; and
determining the drop delay of the flow stream based on the first frequency and the second frequency.

2. The method according to clause 1, wherein the second frequency is the frequency of drop perturbation of the flow stream that is most similar to the image at the first frequency over the detection field.

3. The method according to clause 1, wherein the second frequency is the frequency of drop perturbation of the flow stream that contains one more distinct drop in the detection field than at the first frequency.

4. The method according to clause 1 or 2, wherein the detection field comprises the flow stream upstream from the flow stream break-off point and downstream from the laser irradiation point.

5. The method according to any one of clauses 1 to 4, wherein the second frequency is obtained from a plurality of different drop perturbation frequencies.

6. The method according to clause 5, further comprising capturing one or more images of the flow stream in the detection field at each of the different drop perturbation frequencies.

7. The method according to clause 5, wherein the second frequency is obtained when one or more of the captured images shows an increase of one distinct drop in the detection field.

8. The method according to clause 5, wherein the second frequency is obtained when one or more of the captured images are most similar to the captured image at the first frequency over some detection field.

9. The method according to clause 8, wherein image similarity is determined by minimizing the spatial shift of an image characteristic from the image at the first frequency to the image at the second frequency.

10. The method according to clause 9, wherein the image characteristic is one or more droplets.

11. The method according to clause 9, wherein the image characteristic is the flow stream.

12. The method according to clause 8, wherein image similarity is determined by maximizing the correlation signal between a portion of the image at the frequency and the same portion of the image at the second frequency.

13. The method according to clause 12, wherein the portion of the image comprises 75% or less of image.

14. The method according to clause 12, wherein the portion of the image comprises 25% or less of the image.

15. The method according to clause 12, wherein the portion of the image comprises 10% or less of the image.

16. The method according to clause 12, wherein the portion of the image is the flow stream.

17. The method according to any one of clauses 1 to 16, wherein the detection field comprises the flow stream downstream from a deflection plate, wherein the flow stream is subjected to an electrical charge upstream from the deflection plate.

18. The method according to clause 17, wherein the first frequency is obtained when one or more of the captured images shows deflection of one or more drops in the detection field.

19. The method according to clause 18, wherein the second frequency is obtained from a plurality of different drop perturbation frequencies.

20. The method according to clause 19, further comprising capturing one or more images of the flow stream downstream from the deflection plate at each of the different drop perturbation frequencies.

21. The method according to clause 20, wherein the second frequency is obtained when one or more of the captured images exhibits a maximal stream deflection in the detection field.

22. The method according to clause 21, wherein the first frequency and the second frequency are not determined based on detection of current from the charged flow stream drops.

23. The method according to any one of clauses 1 to 22, further comprising determining the one or more of the amplitude and phase of drop perturbations at each of the different frequencies.

24. The method according to clause 23, wherein the amplitude and/or phase are determined by:
irradiating a flow stream subjected to the oscillating vibration;
detecting first and second light signals along the irradiated flow stream, wherein the first and second light signals are obtained at different positions on a detector; and
calculating a differential signal amplitude between the first signal and second signal.

25. The method according to clause 24, wherein the flow stream is irradiated with a laser.

26. The method according to clause 25, wherein the laser has a beam spot diameter of 100 μm or smaller.

27. The method according to clause 24, wherein the first and second light signals are detected with a position sensing detector.

28. The method according to clause 27, wherein the position detector comprises a photodiode.

29. The method according to clause 28, wherein the position detector comprises 2 or more photodiodes.

30. The method according to clause 29, wherein the position detector is a quadrant photodiode.

31. The method according to any one of clauses 23 to 30, further comprising adjusting one or more of the amplitude and phase of drop perturbations at each of the different frequencies.

32. The method according to clause 31, wherein the method comprises maintaining constant one or more of the amplitude and phase of drop perturbations at each of the different frequencies.

33. The method according to clause 31, wherein the method comprises maximizing the similarity of an image characteristic at each of the different frequencies to a characteristic of the image at the first frequency.

34. The method according to clause 33, wherein the image characteristic is one or more droplets.

35. The method according to clause 33, wherein the image characteristic is the flow stream.

36. The method according to clause 33, wherein the image characteristics at the first frequency and the second frequency are obtained from different portions of the two images.

37. The method according to any one of clauses 1 to 36, further comprising applying an oscillating vibration to a flow nozzle.

38. The method according to clause 37, wherein the oscillating vibration is applied to the flow nozzle by a piezoelectric drop formation transducer.

39. The method according to clause 37, wherein the method comprises applying a plurality of different oscillating vibrations to the flow nozzle.

40. The method according to clause 37, wherein the plurality of different applied oscillating vibrations have different amplitudes and phases.

41. The method according to any one of clauses 1 to 40, further comprising adjusting one or more parameters of the flow cytometer in response to the determined drop delay.

42. The method according to clause 41, wherein the timing of applying an electrical charge to the flow stream is adjusted in response to the determined drop delay.

43. The method according to any one of clauses 1 to 42, wherein the flow stream does not contain beads.

44. The method according to any one of clauses 1 to 42, wherein the flow stream does not contain fluorescent calibration particles.

45. The method according to any one of clauses 1 to 44, wherein the flow stream does not contain a biological sample.

46. The method according to any one of clauses 1 to 45, wherein the flow stream does not contain any biological cells.

47. The method according to any one of clauses 1 to 46, where the drop delay includes an adjusting term to compensate for the spatial difference between the detection field and the location of droplet breakoff 48. The method according to any one of clauses 1 to 46, where the drop delay includes and adjusting term to compensate for the temporal difference between the instant of image acquisition and the instant of droplet breakoff.

49. A system comprising:
an imaging sensor configured to capture one or more images of a flow stream subjected to an oscillating vibration in a detection field of a flow cytometer; and
a processor comprising memory operably coupled to the processor, wherein the memory includes instructions stored thereon to:
obtain a first frequency of drop perturbation of the flow stream;
obtain a second frequency of drop perturbation based on one or more of the captured images; and
determine the drop delay of the flow stream based on the first frequency and the second frequency.

50. The system according to clause 49, wherein the memory further comprises instructions to obtain the second frequency from a plurality of different drop perturbation frequencies.

51. The system according to clause 49, wherein the memory comprises instructions to obtain the second frequency from the plurality of different drop perturbation frequencies when one or more of the captured images shows an increase of one distinct drop in the detection field.

52. The system according to clause 49, wherein the memory comprises instructions to obtain the second frequency from the plurality of different drop perturbation frequencies when one or more of the captured images shows a maximal similarity to the first image over some portion of the detection field.

53. The system according to clause 52, wherein the detection field comprises the flow stream upstream from the flow stream break-off point and downstream from a laser irradiation point.

54. The system according to any one of clauses 49 to 53, wherein the detection field comprises the flow stream downstream from a deflection plate, wherein the flow stream is subjected to an electrical charge upstream from the deflection plate.

55. The system according to clause 54, wherein the memory further comprises instructions to obtain a first frequency when one or more of the captured images shows deflection of one or more drops in the detection field.

56. The system according to clause 55, wherein the memory further comprises instructions to obtain the second frequency from a plurality of different drop perturbations.

57. The system according to clause 56, wherein the memory further comprises instructions to obtain the second frequency when one or more of the captured images exhibits a maximal stream deflection in the detection field.

58. The system according to clause 57, wherein the system is not configured to determine the first frequency and the second frequency based on detection of current from the charged flow stream drops.

59. The system according to any one of clauses 49 to 58, wherein the memory further comprises instructions to determine the amplitude and phase of drop perturbations at each of the plurality of different frequencies.

60. The system according to clause 59, wherein the memory further comprises instructions to adjust the amplitude and phase of drop perturbations at each of the different frequencies.

61. The system according to clause 60, wherein the memory further comprises instructions to maintain constant one or more of the amplitude and phase of drop perturbations at each of the different frequencies.

62. The system according to any one of clauses 49 to 61, further comprising:
 a flow nozzle; and
 a transducer configured to apply an oscillating vibration to the flow nozzle.
63. The system according to clause 62, wherein the transducer is a piezoelectric transducer operably coupled to the flow nozzle.
64. The system according to any one of clauses 49 to 63, further comprising:
 a light source;
 a sensor configured to detect first and second light signals along a vertical axis of the flow stream subjected to the oscillating vibration,
 wherein the memory of the processor includes instructions to calculate a differential signal amplitude between the first signal and second signal.
65. The system according to clause 64, wherein the sensor is positioned to detect forward scattered light from the flow stream.
66. The system according to clause 64, wherein the light source comprises a laser.
67. The system according to clause 64, wherein the sensor comprises a position sensing detector.
68. The system according to clause 67, wherein the sensor comprises a quadrant photodiode.
69. The system according to clause 67, wherein the sensor comprises a wedge detector.
70. The system according to any one of clauses 49 to 69, wherein the system further comprises:
 a flow nozzle comprising a nozzle chamber and a nozzle orifice;
 a flow channel configured to flow from the nozzle orifice comprising an interrogation zone;
 an irradiation source configured to direct a beam of probing light at the flow channel in the interrogation zone from a particular direction; and
 a lens system operably connected to the nozzle chamber and configured to collect light emitted from the nozzle orifice.
71. The system according to clause 70, further comprising one or more deflection plates.
72. The system according to clause 71, further comprising one or more collection tubes.
73. The system according to any one of clauses 49 to 72, wherein the system is configured to be calibrated in the absence of fluorescent beads.
74. A non-transitory computer readable storage medium comprising instructions stored thereon for determining drop delay of a flow stream in a flow cytometer, the instructions comprising:
 algorithm for obtaining a first frequency of drop perturbation of a flow stream subjected to an oscillating vibration;
 algorithm for capturing one or more images in a detection field of the flow stream with an imaging sensor;
 algorithm for obtaining a second frequency of drop perturbation of the flow stream based on one or more of the captured images; and
 algorithm for determining the drop delay of the flow stream based on the first frequency and the second frequency.
75. The computer readable storage medium according to clause 74, wherein the instructions further comprise algorithm for obtaining the second frequency from a plurality of different drop perturbation frequencies.
76. The computer readable storage medium according to clause 75, wherein the instructions further comprise algorithm for obtaining the second frequency from the plurality of different drop perturbation frequencies when one or more of the captured images shows an increase of one distinct drop in the detection field.
77. The computer readable storage medium according to clause 75, wherein the instructions further comprise an algorithm for obtaining the second frequency from the plurality of different drop perturbation frequencies when one or more of the captured images exhibits a maximal similarity to the first image over a portion of the detection field.
78. The computer readable storage medium according to any one of clauses 74 to 77, wherein the detection field comprises the flow stream upstream from the flow stream break-off point and downstream from a laser irradiation point.
79. The computer readable storage medium according to any one of clauses 74 to 78, wherein the detection field comprises the flow stream downstream from a deflection plate, wherein the flow stream is subjected to an electrical charge upstream from the deflection plate.
80. The computer readable storage medium according to clause 74, wherein the instructions further algorithm to obtain a first frequency when one or more of the captured images shows deflection of one or more drops in the detection field.
81. The computer readable storage medium according to clause 80, wherein the instructions further algorithm to obtain the second frequency from a plurality of different drop perturbations.
82. The computer readable storage medium according to clause 80, wherein the instructions further algorithm to obtain the second frequency when one or more of the captured images exhibits a maximal stream deflection in the detection field.
83. The computer readable storage medium according to any one of clauses 74 to 82, wherein the instructions further comprise algorithm for determining one or more of the amplitude and phase of drop perturbations at each of the different frequencies.
84. The computer readable storage medium according to clause 83, wherein the instructions further comprise:
 algorithm for irradiating a vertical axis of the flow stream subjected to the oscillating vibration;
 algorithm for detecting first and second light signals along the laser irradiated flow stream, wherein the first and second light signals are obtained at different times; and
 algorithm for calculating a differential signal amplitude between the first signal and second signal.
85. The computer readable storage medium according to clause 84, wherein the instructions further comprise algorithm for maintaining constant one or more of the amplitude and phase of drop perturbations at each of the different frequencies.
86. The computer readable storage medium according to any one of clauses 74 to 85, wherein the instructions further comprise algorithm for applying an oscillating frequency to a flow nozzle.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of determining drop delay of a flow stream in a flow cytometer, the method comprising:
   obtaining a first frequency (f1) of drop perturbation of a flow stream subjected to an oscillating vibration;
   capturing one or more images of the flow stream in a detection field;
   obtaining a second frequency (f2) of drop perturbation of the flow stream based on one or more of the captured images;
   determining one or more of the amplitude and phase of drop perturbations at the first frequency and the second frequency; and
   determining the drop delay of the flow stream based on the first frequency and the second frequency.

2. The method according to claim 1, wherein the second frequency is the frequency of drop perturbation of the flow stream that is most similar to the image at the first frequency in the detection field.

3. The method according to claim 1, wherein the second frequency is obtained when one or more of the captured images are most similar to the captured image at the first frequency over the detection field.

4. The method according to claim 3, wherein image similarity is determined by minimizing the spatial shift of an image characteristic from the image at the first frequency to the image at the second frequency.

5. The method according to claim 3, wherein image similarity is determined by maximizing the correlation signal between a portion of the image at the frequency and the same portion of the image at the second frequency.

6. The method according to claim 5, further comprising capturing one or more images of the flow stream downstream from a deflection plate at a plurality of different drop perturbation frequencies and the second frequency is obtained when one or more of the captured images exhibits a maximal stream deflection in the detection field.

7. The method according to claim 1, wherein the amplitude and phase of drop perturbations are determined by:
   irradiating a flow stream subjected to the oscillating vibration;
   detecting first and second light signals along the irradiated flow stream, wherein the first and second light signals are obtained at different positions on a detector; and
   calculating a differential signal amplitude between the first signal and second signal.

8. The method according to claim 7, further comprising adjusting the amplitude and phase of drop perturbations at each of the different frequencies.

9. The method according to claim 8, wherein the method comprises maintaining a constant amplitude and phase of drop perturbations at each of the different frequencies.

10. The method according to claim 1, further comprising applying one or more oscillating vibrations having different amplitudes and phases to a flow nozzle.

11. A system comprising:
   an imaging sensor configured to capture one or more images of a flow stream subjected to an oscillating vibration in a detection field of a flow cytometer; and
   a processor comprising memory operably coupled to the processor, wherein the memory includes instructions stored thereon to:
      obtain a first frequency of drop perturbation of the flow stream;
      obtain a second frequency of drop perturbation based on one or more of the captured images;
      determine one or more of the amplitude and phase of drop perturbations at each of the first frequency and the second frequency; and
      determine the drop delay of the flow stream based on the first frequency and the second frequency.

12. The system according to claim 11, wherein the memory comprises instructions to obtain the second frequency from the plurality of different drop perturbation frequencies when one or more of the captured images shows the frequency of drop perturbation of the flow stream that is most similar to the image at the first frequency in the detection field.

13. The system according to claim 11, further comprising deflection plates, wherein the detection field comprises the flow stream downstream from a deflection plate and wherein the flow stream is subjected to an electrical charge upstream from the deflection plate and
   wherein the memory further comprises one or more of:
      instructions to obtain a first frequency when one or more of the captured images shows deflection of one or more drops in the detection field;
      instructions to obtain the second frequency from a plurality of different drop perturbations; and
      instructions to obtain the second frequency when one or more of the captured images exhibits a maximal stream deflection in the detection field.

14. A non-transitory computer readable storage medium comprising instructions stored thereon for determining drop delay of a flow stream in a flow cytometer, the instructions comprising:
   algorithm for obtaining a first frequency of drop perturbation of a flow stream subjected to an oscillating vibration;
   algorithm for capturing one or more images in a detection field of the flow stream with an imaging sensor;
   algorithm for obtaining a second frequency of drop perturbation of the flow stream based on one or more of the captured images;
   algorithm for determining one or more of the amplitude and phase of drop perturbations at the first frequency and the second frequency; and
   algorithm for determining the drop delay of the flow stream based on the first frequency and the second frequency.

* * * * *